United States Patent
Andre et al.

(10) Patent No.: US 9,157,119 B2
(45) Date of Patent: Oct. 13, 2015

(54) METHODS FOR DIAGNOSING SKIN DISEASES

(75) Inventors: Catherine Andre, Saint Brieuc des Iffs (FR); Sandrine Planchais, Chateaubriant (FR); Eric Guaguere, La Madeleine (FR)

(73) Assignees: CENTRE NATIONAL DE LA RECHERCHE SCIENTIFIQUE (C.N.R.S.), Paris (FR); UNIVERSITE DE RENNES 1, Rennes Cedex (FR)

( * ) Notice: Subject to any disclaimer, the term of this patent is extended or adjusted under 35 U.S.C. 154(b) by 0 days.

(21) Appl. No.: 13/510,620

(22) PCT Filed: Nov. 16, 2010

(86) PCT No.: PCT/EP2010/067569
§ 371 (c)(1),
(2), (4) Date: Nov. 30, 2012

(87) PCT Pub. No.: WO2011/061184
PCT Pub. Date: May 26, 2011

(65) Prior Publication Data
US 2013/0065775 A1  Mar. 14, 2013

Related U.S. Application Data

(60) Provisional application No. 61/261,903, filed on Nov. 17, 2009.

(30) Foreign Application Priority Data

Nov. 17, 2009  (EP) .................................... 09306106

(51) Int. Cl.
C12Q 1/68 (2006.01)

(52) U.S. Cl.
CPC ........ *C12Q 1/6883* (2013.01); *C12Q 2600/156* (2013.01)

(58) Field of Classification Search
None
See application file for complete search history.

(56) References Cited

U.S. PATENT DOCUMENTS 7,799,530 B2 * 9/2010 Iakoubova et al. ........... 435/6.13
2007/0014776 A1 * 1/2007 Gimeno et al. .............. 424/94.2

OTHER PUBLICATIONS

Guaguere et al. Abstract P35, p. 805, Journal of Investigative Dermatology (2009) 129, 792-809 and & Annual Congress of the French-Speaking-Society-For-Dermatological-Research; Toulouse, France; Sep. 12, 2088-Sep. 1.*
Toulza et al. Genome Biol. 2007;8(6):R107.pp. 1-23.*

* cited by examiner

*Primary Examiner* — Stephanie K Mummert
*Assistant Examiner* — Aaron Priest
(74) *Attorney, Agent, or Firm* — Patterson & Sheridan, LLP

(57) ABSTRACT

The present invention relates to methods for diagnosing cornification disorders and metabolic diseases. More specifically, the present invention relates to an in vitro method for diagnosing and/or predicting a cornification disorder in a subject, comprising determining the presence or the absence of a genetic variation in the Patatin-like phospholipase domain-containing protein 1 (PNPLA1) gene sequence in a biological sample from said subject, as compared with the PNPLA1 gene sequence of a healthy non-carrier subject, wherein the presence of said genetic variation indicates that said subject suffers from or is at risk of suffering from said cornification disorder. The method according to the invention allows for example diagnosing ichthyosis in dogs of the Golden Retriever breed.

8 Claims, 2 Drawing Sheets

A.

SEQ ID NO: 1   1416 CCAGCAAGCCTCATGCAATGGGAAACC--------CTACTGAAGACTCCAGTTGGATGAGCAA 1480
                    ||||||||||||||||||||||||||||        ||||||||||||||||||||||||||||
SEQ ID NO: 3   1416 CCAGCAAGCCTCATGCAATGGGAA----TACTACTACTGAAGACTCCAGTTGGATGAGCAA 1485

Nucleotides          Nucleotides
                              1445-1447            1445-1452

B.

SEQ ID NO: 2   451 QSQAPLASSKPEGTTPLVNVKEATSKPHAMGNPTEDSSWMSKVFKKNKQKTSSTRKGFPRHPRSK 515
                    ||||||||||||||||||||||||||||||
SEQ ID NO: 4   451 QSQAPLASSKPEGTTPLVNVKEATSKPHAMGILLLLKTPVG 491

SEQ ID NO: 2   516 KTGGKVQSAPCPLDFTLLSTSETVWVTYRPHPSQIQEHSCPEEAVNQERT 565
SEQ ID NO: 4   491                                                    491

FIG.1

METHODS FOR DIAGNOSING SKIN DISEASES

FIELD OF THE INVENTION

The present invention relates to methods for diagnosing and predicting skin diseases, in particular for diagnosing and predicting cornification disorders such as ichthyosis in dogs.

BACKGROUND OF THE INVENTION

Ichthyosis is a skin disease that is wide-spread among dogs of the Golden Retriever breed. The symptoms of ichthyosis include excessive scaling of large, variably pigmented flakes of skin in otherwise healthy dogs. The condition affects young dogs of either sex and is characterised by symmetrical, predominantly ventro-lateral scaling and hyperpigmentation of the trunk.

An article reporting 50 cases of ichthyosis in dogs of Golden Retriever breed was first published in 2007 (Guaguere et al., 2007 Veterinary Dermatology. 18:382-383). A genetic aetiology, with single-trait autosomal recessive mode of inheritance, was then proposed in 2008 (Mauldin et al., 2008 Vet Pathol. 45:174-80; Cadiergues et al., 2008 Vet Dermatol. 19:120-9). Dermatological signs of Golden Retriever ichthyosis include a mild to moderate or severe generalised scaling with initially small to large whitish scales and progressively blackish scales. The ventral glabrous skin is hyperpigmented and rough, similar to sandpaper.

Histopathological features are characterised by moderate to severe laminated or compact orthokeratotic epidermal hyperkeratosis composed of many keratin layers, without significant involvement of the stratum granulosum. Epidermis has a pleated appearance, and diffuse epidermal melanin pigmentation was observed in most cases. Keratinocytes from the basal and spinous layers seem to form agglutinated cell masses. Some keratinocytes with lipidic vacuoles are regularly visible in the stratum granulosum. Rete ridges of the epidermis give a pleated appearance resembling a garland (Guaguere et al., 2009, J Small Anim Pract. 50:227-35). Ultrastructural findings reveal laminated or compact keratin layers and numerous persistent corneodesmosomes within the stratum corneum. Melanosomes are found throughout the epidermis, as well as lipidic vacuoles within the stratum corneum.

In summary, the histopathological and ultrastructural characteristics strongly suggest that Golden Retriever ichthyosis is a non epidermolytic, retention ichthyosis, caused by absence of corneodesmosomal degradation, transmitted through an autosomal recessive mode (Guaguere et al., 2009, J Small Anim Pract. 50:227-35).

In addition to dogs of Golden Retriever breed, ichthyosis is also found in other dogs such as dogs of Cavalier King Charles Spaniel, Irish Soft Coated Wheaten Terrier, Collie, American Bulldog, American Staffordshire Terrier, Dobermann, Rottweiler, Australian Terrier, Manchester Terrier, Boston Terrier, West Highland White Terrier, Norfolk terrier and Jack Russel terrier breed.

Ichthyosis is also found in human beings. In human, ichthyosis is a family of generalized skin disorders wherein the patients have dry, thickened, scaly or flaky skin. The severity of symptoms can vary enormously, from the mildest types such as ichthyosis vulgaris which may be mistaken for normal dry skin, up to life-threatening conditions such as harlequin type ichthyosis. Some types of ichthyoses occur in isolation without associated abnormalities (e.g. ichthyosis vulgaris, X-linked ichthyosis, bullous congenital, ichthyosiform erythroderma and ichthyosis lamellaris), while other types of ichthyoses are part of a syndrome that involves multiple organs (e.g. Netherton syndrome, Dorfman-Chanarin syndrome, Refsum's disease and Sjögren-Larsson syndrome). Apart from acquired ichthyosis due to a systemic disease such as e.g. leprosy, hypothyroidism, lymphoma or AIDS, all types of ichthyosis appear to be inherited diseases. For instance, lamellar ichthyosis, Refsum's disease and Sjögren-Larsson syndrome are autosomal recessive diseases.

Genes at least partially associated with some types of human ichthyoses have been identified (see e.g. Akiyama and Shimizu. 2008 Exp Dermatol. 17:373-82; Oji. V, 2010, Hautarzt, 61(10):891-902). At present, a dozen of genes have been identified but all human cases are far from having a known molecular defect. In dogs, the genetic defect has been identified for 2 breeds segregating ichthyosis, namely the Norfolk terrier and the Jack Russel terrier. In the Norfolk terrier breed, a mutation in the Keratin 10 gene was identified in 2005 (Credille et al., 2005 Br J. Dermatol. 153:51-8.). In the Jack Russel terrier breed, a mutation in the TGM1 gene was found (Credille et al., Br J Dermatol. 2009 161:265-72 2009).

However, the genes involved in Golden Retriever ichthyosis, in other affected dog breeds, and in several human familial or sporadic cases of ichthyosis, still remain to be identified.

Currently, there is no method for predicting the risk of suffering from Golden Retriever ichthyosis and the diagnosis requires a skin biopsy and an histopathologic analysis. Such a method would be of great value not only in the field of veterinary medicine, but also in the field of human medicine.

Among dogs, the Golden Retriever breed is a very popular breed with an estimated population of 8000 births per year in France. A method for predicting the risk of suffering from ichthyosis would allow selecting pups which are neither at risk of developing the disease, nor carrier of the disease. It would also allow selecting dogs suitable for reproduction.

There is thus a need for a method for diagnosing ichthyosis and/or predicting the risk of suffering from ichthyosis or transmitting the disease to the progeny.

DESCRIPTION OF THE INVENTION

The present invention arises from the finding that mutations in the PNPLA1 gene are involved in the development of ichthyosis.

The inventors collected more than 300 blood and 30 tissue samples from Golden Retrievers, together with the pedigrees of the dogs. Forty Golden Retrievers, twenty of which suffered from ichthyosis and twenty of which were healthy, were selected for a genetic analysis. These forty dogs were as unrelated as possible, and have all had a histopathologic diagnosis according to the criteria set forth in Guaguere et al. (2009, J Small Anim Pract. 50:227-35). The DNA of these dogs was extracted and genotyped using the canine Affymetrix SNP chips. A genetic association study was carried out. It was found that a region of 7 megabases located on chromosome 12, and which comprised 217 genes, was associated with ichthyosis. Based on the putative function of these genes, three candidate genes were selected for further analysis.

One of these candidate genes corresponded to the Patatin-like phospholipase domain-containing protein 1 (PNPLA1) gene. This gene belongs to the adiponutrin gene family and is not well characterized. Proteins of the adiponutrin family are believed to have both lipolytic and lipogenic properties (Johansson et al., 2009, PLoS One. 4:e5327).

The inventors identified one mutation in the PNPLA1 gene which perfectly segregated with ichthyosis. This mutation is a replacement of three nucleotides (namely nucleotides 1445 to 1447 of SEQ ID NO: 1) with eight nucleotides consisting of TACTACTA. This mutation leads to the presence of a premature stop codon, and consequently to the synthesis of a truncated protein which is assumed to be biologically inactive or to harbour an activity which is different of its normal biological activity.

The PNLPA1 gene of 100 Golden Retrievers suffering from ichthyosis was sequenced, and all of them comprised a mutation in both alleles of the PNPLA1 gene. The PNLPA1 gene of 100 healthy Golden Retrievers was also sequenced. 18 of them comprised two wild-type alleles of the PNPLA1 gene, whereas 82 of them comprised a mutation in only one of the two alleles of the PNPLA1 gene, the other allele being a wild-type allele.

The inventors have thus found that Golden Retrievers suffering from ichthyosis displayed a mutation in both alleles of the PNPLA1 gene, whereas healthy Golden Retrievers displayed either two wild-type alleles of the PNPLA1 gene, or one wild-type allele together with one mutated allele. Since ichthyosis is known to be a genetic disease with single-trait autosomal recessive mode of inheritance, this result shows that PNPLA1 is the gene that causes ichthyosis in Golden Retrievers.

In addition, the inventors have shown that PNPLA1 is specifically expressed in skin and to a lower extent in the brain and the intestine, and that its biological function is relevant for the disease. This gene was not previously known as being involved in skin diseases.

Therefore, the inventors have identified a new gene responsible for the development of ichthyosis, namely PNPLA1.

Method of Diagnosing and/or Predicting a Skin Disease or a Metabolic Disease

The present invention thus relates to the use of at least one genetic variation in the PNPLA1 gene as a marker for diagnosing whether a subject suffers from or is at risk of suffering from a skin disease or a metabolic disease.

More specifically, the invention is directed to an in vitro method for diagnosing and/or predicting a skin disease or a metabolic disease in a subject, comprising or consisting of the step of determining the presence or the absence of a genetic variation in the Patatin-like phospholipase domain-containing protein 1 (PNPLA1) gene sequence in a biological sample from said subject, as compared with the PNPLA1 gene sequence of a healthy non-carrier subject, wherein the presence of said genetic variation indicates that said subject suffers from or is at risk of suffering from said skin disease or metabolic disease, or is at risk of transmitting said disease to its progeny.

The method may further comprise, before the step of determining, the step of obtaining or providing a biological sample from said subject.

In the context of the invention, a genetic variation may be homozygous or heterozygous. A homozygous genetic variation means that the same genetic variation is present on both alleles of the gene carrying said genetic variation. A heterozygous genetic variation means on the contrary that said genetic variation is only present on one allele of the gene carrying said genetic variation.

In the case of an autosomal recessive disease such as e.g. inherited ichthyosis, the presence of said genetic variation in both alleles of said PNPLA1 gene indicates that said subject suffers from or is at risk of suffering from said skin disease or metabolic disease. Conversely, the presence of said genetic variation in only one of the two alleles of said PNPLA1 gene indicates that said subject is a healthy carrier of said skin disease or metabolic disease. The absence of said genetic variation indicates that said subject is a healthy non-carrier of said skin disease or metabolic disease.

an in vitro method for diagnosing and/or predicting a skin disease or a metabolic disease in a subject, comprising or consisting of determining the presence or the absence of a homozygous genetic variation in the Patatin-like phospholipase domain-containing protein 1 (PNPLA1) gene sequence in a biological sample from said subject, as compared with the PNPLA1 gene sequence of a healthy non-carrier subject, wherein the presence of said homozygous genetic variation indicates that said subject suffers from or is at risk of suffering from said skin disease or metabolic disease;

an in vitro method for identifying a subject which is healthy carrier of a skin disease or a metabolic disease, comprising or consisting of determining the presence or absence of an heterozygous genetic variation in the PNPLA1 gene sequence in a biological sample from said subject, as compared with the PNPLA1 gene sequence of a healthy non-carrier subject, wherein the presence of said heterozygous genetic variation indicates that said subject is a healthy carrier of said skin disease or metabolic disease; and an in vitro method for identifying a subject which is healthy non-carrier of a skin disease or a metabolic disease, comprising or consisting of determining the presence or absence of an heterozygous genetic variation in the PNPLA1 gene sequence in a biological sample from said subject, as compared with the PNPLA1 gene sequence of a healthy non-carrier subject, wherein the absence of said heterozygous genetic variation indicates that said subject is a healthy non-carrier of said skin disease or metabolic disease.

In the frame of the present invention, the "subject" is a mammal such as e.g. a dog or a human being.

The subject can for example be a dog of Golden Retriever breed or of Golden Retriever type. Indeed, Golden Retrievers are particularly susceptible to ichthyosis. As used herein, the term "Golden Retriever" refers to a dog belonging to the breed described in the Fédération Cynologique Internationale (FCI) standard n° 111 (published on Jun. 24, 1987 and updated on Jan. 29, 1999). Golden retrievers are classified under group 8, section 1, of the FCI classification. As used herein, the term "Golden Retriever type" refers to a dog without pedigree having at least one Golden Retriever in his parents or grand-parents.

Ichthyosis has also been found in dogs of other breeds than of Golden Retriever breed, including dogs of the following breeds: Cavalier King Charles Spaniel (FCI standards Nos. 128 and 136), Irish Soft Coated Wheaten Terrier (FCI standard No. 40), Collies (as used herein, this term includes the Bearded Collie, FCI standard No. 271; the Border Collie, FCI standard No. 297; the Collie Rough, FCI standard No. 156; and the Collie Smooth, FCI standard No. 296), American Bulldog (breed registry held by the American Bulldog Association), American Staffordshire Terrier (FCI standard No. 286), Dobermann (FCI standard No. 143), Rottweiler (FCI standard No. 147), Australian Terrier (FCI standard No. 8), Manchester Terrier (FCI standard No. 71), Boston Terrier (FCI standard No. 140) and West Highland White Terrier (FCI standard No. 85), Pomeranian dog, Griffon (as used herein, this term includes Grand Griffon Vendeen, FCI standard No. 282; Medium Griffon Vendeen, FCI standard No. 19; Blue Gascony Griffon, FCI standard No. 32; Fawn Brittany Griffon, FCI standard No. 66; Griffon nivernais, FCI standard No. 17; French wire-haired Korthals Pointing Griffon, FCI standard No. 107; Belgian Griffon, FCI standard No.

81; Brussels Griffon, FCI standard No. 80; and Small Brabant Griffon, FCI standard No. 82). Therefore, the subject can for example be a dog of any breed. In particular, the subject can be a dog of any of the above breeds, or a dog without pedigree having at least one of the above breeds in his parents or grand-parents.

In addition, dogs of Golden Retriever breed are sometimes crossed with dogs of Labrador Retriever breed (FCI standard No. 122) or of other retriever breeds such as Curly Coated Retriever (FCI standard No. 110) and Cheasapeake Bay Retriever (FCI standard No. 263). Therefore, the subject can also be a dog of retriever breed (preferably of Labrador Retriever breed), or a dog without pedigree having at least one dog of retriever breed (preferably of Labrador Retriever breed) in his parents or grand-parents.

As used herein, the term "skin disease" refers to any type of inherited dermatologic disease involving the skin. The skin disease preferably corresponds to a cornification disorder. Cornification disorders are a group of diseases well known to the one skilled in the art (for a review, see Oji. V, 2010, Hautarzt, 61(10):891-902). In the context of the present invention, the term "cornification disorder" includes diseases such as ichthyosis (including e.g. lamellar ichthyosis and epidermolytic hyperkeratosis), psoriasis, hyperkeratosis and eczema.

Such a cornification disorder is preferably ichthyosis.

In a preferred embodiment, the skin disease is a form of ichthyosis that is found in dogs (especially in Golden Retrievers). The ichthyosis may also be a form of ichthyosis that is found in human beings. In human, there are many different types of inherited ichthyoses that are classified according to clinical and genetic criteria (see e.g. Bale and DiGiovanna, 1997, Adv Dermatol. 12:99-114; Oji. V, 2010, Hautarzt, 61(10):891-902). The ichthyosis may be an ichthyosis occurring in isolation such as ichthyosis vulgaris, X-linked ichthyosis, bullous congenital ichthyosiform erythroderma (also known as epidermolytic hyperkeratosis), nonbullous congenital ichthyosiform erythroderma, ichthyosis lamellaris, Harlequin type ichthyosis, Ichthyosis bullosa of Siemens, Ichthyosis hystrix and Carvajal syndrome. Alternatively, the ichthyosis may be part of a syndrome that involves multiple organs such as Netherton syndrome, Dorfman-Chanarin syndrome, Refsum's disease, Sjögren-Larsson syndrome, CHILD syndrome, Conradi-Hünermann syndrome, Darier's disease, erythrokeratodermia variabilis, ichthyosis follicularis, keratitis-ichthyosis-deafness syndrome, Rud syndrome and trichothiodystrophy.

As used herein the term "PNPLA1 gene" refers to the PNPLA1 gene (including the 5' regulatory region, the promoter, the introns, the exons and the 3' regulatory region). As known to one skilled in the art, a gene includes both transcribed and untranscribed regions. The transcribed region may include introns, which are spliced out of the mRNA, and 5'- and 3'-untranslated (UTR) sequences along with the protein coding sequences (exons). Accordingly, as used herein, the genomic sequence of the PNPLA1 gene contains 5'- and 3'-UTR sequences, introns and exons. The genomic sequence of the dog PNPLA1 gene is represented herein by SEQ ID NO: 5.

As used herein, the term "PNPLA1 cDNA" refers to the coding sequence of the PNPLA1 gene lacking introns. As known to one skilled in the art, several different cDNAs may be transcribed from a given gene, depending on alternative splicing. The term PNPLA1 cDNA is meant to encompass all alternative splice variants. The dog PNPLA1 cDNA encompasses for example the cDNAs of sequence SEQ ID Nos. 1 and 3, which are transcribed in skin.

The terms "PNPLA1 gene" and "PNPLA1 cDNA" encompass genes and cDNAs of any mammalian origin. Mammalian PNPLA1 genes and cDNAs are well-known to the skilled in the art and include, e.g., those of *Homo sapiens* (GeneID: 285848, chromosome 6; Location 6p21.31), *Pan troglodytes* (GeneID: 471991, chromosome 6), *Bos Taurus* (GeneID: 786, chromosome 23), *Equus caballus* (GeneID: 100063661, chromosome 20), *Mus musculus* (GeneID: 433091, chromosome 17, Location: 17 A3.3) and *Rattus norvegicus* (GeneID: 361812, chromosome 20, Location: 20p12). More specifically, the sequence of the human PNPLA1 gene is shown on NCBI accession No. NC_000006.11 (36210945 . . . 36276372).

In the context of the present invention, the terms "genetic variation", "polymorphism" and "mutation" are used indifferently and contemplate single nucleotide substitutions, insertions, deletions and substitutions of one or more nucleotides, repetitive sequences (such as microsatellites), and the total or partial absence of genes. The genetic variation according to the invention may for example correspond to a single nucleotide polymorphism (SNP). The term "single nucleotide polymorphism" in the context of the present invention includes single base nucleotide substitutions, deletions or insertions. The SNP may be, e.g., a biallelic marker. The genetic variation may for example correspond to a loss of function mutation, i.e. a mutation leading to partial or complete loss of the biological activity of the polypeptide encoded by the mutated gene.

In a specific embodiment of the in vitro method for diagnosing and/or predicting a skin disease or a metabolic disease in a subject according to the invention, genetic variation in the PNPLA1 gene sequence leads either to a lack of synthesis of PNPLA1 protein, or to the synthesis of a non-functional PNPLA1 protein.

In a preferred embodiment of the invention, the subject is a dog.

Further, in a particularly preferred embodiment, the genetic variation is a replacement, in the dog PNPLA1 gene, of the nucleotides at position 1445 to position 1447 of SEQ ID NO: 1 with eight nucleotides consisting of TACTACTA (see FIG. 1A). In order to make the reading easier, the sequence of a dog PNPLA1 gene comprising a replacement of nucleotides 1445 to 1447 of SEQ ID NO: 1 with eight nucleotides consisting of TACTACTA will be called "del3ins8 allele". The del3ins8 mutation is located within the eighth exon of the PNPLA1 gene.

As defined above, the cDNA sequence of the PNPLA1 gene consists of the exons of the genomic sequence. Accordingly, a determined nucleotide position of the cDNA sequence corresponds to a determined position of the genomic sequence. In the context of the invention, the nucleotides at position 1445 to 1447 of the PNPLA1 cDNA sequence of SEQ ID NO: 1 correspond to the nucleotides at position 40019 to 40021 of the PNPLA1 gene sequence of SEQ ID NO: 5.

As known from one skilled in the art, introns of a gene may display numerous polymorphisms between subjects. Accordingly, a determined nucleotide position of the cDNA sequence of a gene may not correspond exactly to the same nucleotide position of the genomic sequence of the gene from a subject to another. Such a correspondence is nevertheless easily determined by one skilled in the art.

In a particular embodiment, said genetic variation is determined on the transcript or the antisens strand of the PNPLA1 gene. As known from one skilled in the art, the sequence of the antisens strand of a gene is complementary to the sequence of the coding strand. This coding strand is transcribed in RNA, which may be spliced to form mRNA. The sequence of said mRNA is complementary to the sequence corresponding to the juxtaposition of the exons sequences contained in the coding strand. Accordingly, in the context of the invention, the del3ins8 allele as defined above corresponds to the presence of a nucleotide sequence consisting of TAGTAGTA on the antisense strand sequence of the PNPLA1 gene.

As used herein, the term "diagnosing" includes determining, monitoring, confirming, subclassifying and predicting a disease, disorder, complication, or risk in a subject. As used herein, the term "predicting" refers to making a finding that a subject has a significantly enhanced probability of developing a disease. The methods according to the invention may be carried out either on biological samples obtained after birth of the subject being diagnosed, or on biological samples obtained from an embryo in the frame of a pre-natal diagnostic test.

In the context of the invention, the term "healthy non-carrier" refers to a subject that is not and will not be affected by a disease and that will never transmit the disease to its progeny. Typically, according to the invention, a dog which is healthy non-carrier of ichthyosis is homozygous for the wild-type allele of the PNPLA1 gene. In particular, its genome does not comprise any copy of the del3ins8 allele of the PNPLA1 gene.

In the context of the invention, the term "healthy carrier" refers to a subject that can transmit the disease to its progeny but which does not develop the disease. Typically, according to the invention, a dog which is healthy carrier of Ichthyosis only carries one del3ins8 allele. As ichthyosis is an autosomal recessive disease, said dog will not develop the disease. However, it has one chance on two to transmit the allele displaying the genetic variation to its progeny. Accordingly, if the progeny also receives an allele displaying the genetic variation from the other parent, which can either be a healthy carrier of ichthyosis or homozygous for the del3ins8 allele, said progeny will be affected by ichthyosis.

As used herein, the term "biological sample" means a substance of biological origin. In particular the biological sample comprises DNAs, RNAs and/or proteins from the subject to be diagnosed. Examples of biological samples include but are not limited to blood and components thereof such as plasma and subpopulations of blood cells, serum, saliva, mouth epithelial cells, and organs or tissues such as skin, intestine, brain, kidney, liver, heart and lung.

Numerous methods allowing determining the presence of a genetic variation in a biological sample are well known from the one skilled in the art. These methods include, without being limited to, sequencing (e.g. automated sequencing, microsequencing and pyrosequencing), restriction fragment length polymorphism (RFLP), single-strand conformation polymorphism (SSCP), denaturing gradient gel electrophoresis (DGCE), temperature gradient gel electrophoresis (TGGE), hybridization methods with DNA probes specific of said genetic variation (e.g. comparative genomic hybridization (CGH), matrix-CGH, array-CGH, oligonucleotide arrays and representational oligonucleotide microarray (ROMA)), high-throughput technologies for genotyping (for example using Affymetrix SNP chips), and amplification methods such as quantitative polymerase chain reaction (qPCR) or a polymerase chain reaction (PCR) followed by sequencing, microsequencing, pyrosequencing or RFLP. The presence of a genetic variation can also be determined at the protein level, e.g. by an ELISA assay carried out with an antibody specifically detecting the mutated protein.

Polynucleotides, Probes, Primers, Polypeptides, Antibodies and Uses Thereof

The inventors of the present invention have identified the exon/intron boundaries of the dog PNPLA1 gene (SEQ ID NO: 5), which were differently annotated in the two public sequence databases UCSC and Ensembl. As a consequence, they have identified the correct sequence of the dog PNPLA1 cDNA (SEQ ID NO: 1) as expressed in skin and of the corresponding dog PNPLA1 protein (SEQ ID NO: 2). The inventors have also identified a mutant allele of the PNPLA1 gene, namely the del3ins8 allele (SEQ ID Nos: 3 and 4). Finally, the inventors have identified the biological function of the PNPLA1 protein, i.e., it avoids excessive scaling of the skin and allows a perfect lipidic balance in the skin.

Therefore, the present invention is directed to:
a) an isolated polynucleotide comprising or consisting of a sequence at least 93, 94, 95, 96, 97, 98, 99 or 100% identical to the sequence of SEQ ID NO: 1;
b) an isolated polynucleotide comprising or consisting of a sequence at least 80, 90, 95, 96, 97, 98, 99 or 100% identical to the sequence of SEQ ID NO: 3, wherein said polynucleotide comprises nucleotides 1445 to 1452, 1444 to 1452, 1444 to 1453, 1443 to 1455, 1440 to 1457 or 1435 to 1462 of SEQ ID NO: 3;
c) an isolated polynucleotide comprising or consisting of a sequence complementary to the sequence of (a) or (b).
d) an isolated polynucleotide comprising or consisting of at least, at most and/or about 12, 15, 25, 50, 100, 250, 500, 1000, 1500, 1600 or 1700 consecutive nucleotides of the polynucleotide of (a), (b) or (c);
e) an isolated polypeptide comprising or consisting of a sequence at least 92, 93, 94, 95, 96, 97, 98, 99 or 100% identical to the sequence of SEQ ID NO: 2;
f) an isolated polypeptide comprising or consisting of a sequence at least 80, 90, 95, 96, 97, 98, 99 or 100% identical to the sequence of SEQ ID NO: 4, wherein said polypeptide comprises amino acids 482 to 491 of SEQ ID NO: 4; and
g) an isolated polypeptide comprising or consisting of at least, at most and/or about 15, 25, 50, 100, 150, 200, 250, 300, 350, 400, 450, 500 or 550 consecutive amino acids of the polypeptide of (e) or (f).

Such polynucleotides and polypeptides can easily be obtained by the skilled in the art. The polynucleotides according to the invention can for example be obtained by cloning the PNPLA1 gene or cDNA using suitable primers. The polynucleotide can then be cloned into a vector, preferably into an expression vector. The expression vector may then be introduced into a host cell in order to produce the polypeptide according to the invention.

By a polynucleotide having a sequence at least, for example, 95% "identical" to a query sequence of the present invention, it is intended that the sequence of the polynucleotide is identical to the query sequence except that the sequence may include up to five nucleotide alterations per each 100 nucleotides of the query sequence. In other words, to obtain a polynucleotide having a sequence at least 95% identical to a query sequence, up to 5% (5 of 100) of the nucleotides of the sequence may be inserted, deleted, or substituted with another nucleotide. In other terms, the sequences should be compared on their entire length (i.e. by preparing a global alignment). For example, a first polynucleotide of 100 nt that is comprised within a second polynucleotide of 200 nt is 50% identical to said second polynucleotide. The needle program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. Preferably, the percentage of identity in accordance with the invention is calculated using the needle program with a "Gap open" parameter equal to 10.0, a "Gap Extend" parameter equal to 0.5, and a Blosum 62 matrix. The needle program is for example available on the ebi.ac.uk World Wide Web site.

"Isolated polynucleotide" refers herein to both RNA and DNA, including cDNA, genomic DNA, and synthetic DNA. Polynucleotides can have any three-dimensional structure. A polynucleotide can be double-stranded or single-stranded (i.e., a sense strand or an antisense strand). Non-limiting examples of polynucleotides include genes, gene fragments, exons, introns, messenger RNA (mRNA), transfer RNA (tRNA), ribosomal RNA, siRNA, micro-RNA, ribozymes, cDNA, recombinant polynucleotides, and branched polynucleotides. A polynucleotide may contain unconventional or modified nucleotides. Isolated polynucleotides according to the invention may be purified or recombinant.

The polynucleotides, primers and probes according to the invention may be of any length, e.g. at least, at most and/or about 12, 15, 18, 25, 50, 100, 250, 500 or 1000 nucleotides long. More specifically, they may comprise or consist of a contiguous span of the PNPLA1 gene of at least, at most and/or about 12, 15, 18, 25, 50, 100, 250, 500 or 1000 nucleotides. Preferably, primers and probes according to the invention consist of at least 18 nucleotides.

Fragments of the PNPLA1 gene or of the PNPLA1 cDNA are useful as primers or probes for detecting a genetic variation in the PNPLA1 gene, e.g. by sequencing, hybridization methods and/or amplification methods.

Therefore, the invention pertains to the use of an isolated polynucleotide comprising or consisting of a contiguous span of at least 12 nucleotides of a PNPLA1 gene or of a PNPLA1 cDNA for diagnosing and/or predicting a skin disease or a metabolic disease in a subject, and/or for identifying a subject which is a healthy carrier or a healthy non-carrier of said disease. When a dog is to be diagnosed, said isolated polynucleotide may for example comprise or consist of a contiguous span of at least 12 nucleotides of SEQ ID NO: 1, SEQ ID NO: 3, SEQ ID NO: 5 or sequences complementary thereto.

A preferred embodiment of the invention is directed to an isolated probe or primer suitable for specifically identifying and/or amplifying the del3ins8 mutation comprising or consisting of a contiguous span of at least 12 nucleotides of a sequence selected from the group of SEQ ID NO: 1, SEQ ID NO: 3, SEQ ID NO: 5 and sequences complementary thereto, wherein said contiguous span comprises nucleotide positions 1445 to 1447 of SEQ ID NO: 1, nucleotide positions 1445 to 1452 of SEQ ID NO: 3, or nucleotide positions complementary thereto. For the sake of completeness, when the sequence of SEQ ID NO: 5 is used as a reference, said contiguous span comprises nucleotide positions 40019 to 40021 of SEQ ID NO: 5, or nucleotide positions complementary thereto.

As used herein, a "probe" refers to an oligonucleotide capable of binding in a base-specific manner to a complementary strand of polynucleotide. Isolated probes according to the invention may be purified or recombinant. They may be labelled with a detectable moiety, i.e. a moiety capable of generating a detectable signal, such as a radioactive, calorimetric, fluorescent, chemiluminescent or electrochemiluminescent signal. Numerous such detectable moieties are known in the art. By way of example, the moiety may be a radioactive compound or a detectable enzyme (e.g., horseradish peroxidase). The probe may for example correspond to a TaqMan© probe.

As used herein, the term "primer" refers to an oligonucleotide which is capable of annealing to a target sequence and serving as a point of initiation of DNA synthesis under conditions suitable for amplification of the primer extension product which is complementary to said target sequence. The primer is preferably single stranded for maximum efficiency in amplification. Preferably, the primer is an oligodeoxyribonucleotide. The length of the primer depends on several factors, including temperature and sequence of the primer, but must be long enough to initiate the synthesis of amplification products. Preferably the primer is from 10 to 35 nucleotides in length. A primer can further contain additional features which allow for detection, immobilization, or manipulation of the amplified product. The primer may furthermore comprise covalently-bound fluorescent dyes, which confer specific fluorescence properties to the hybrid consisting of the primer and the target-sequence or non covalently-bound fluorescent dyes which can interact with the double-stranded DNA/RNA to change the fluorescence properties. Fluorescent dyes which can be used are for example SYBR-green or ethidium bromide.

Another preferred embodiment of the invention is directed to an isolated primer comprising or consisting of:
  a contiguous span of at least 12 nucleotides of a sequence selected from the group of SEQ ID NO: 1, SEQ ID NO: 3, SEQ ID NO: 5, wherein the 3' end of said primer is located at, or at most 10, 9, 8, 7, 6, 5, 4, 3, 2 or 1 nucleotide(s) upstream of the location of the del3ins8 mutation;
  a contiguous span of at least 12 nucleotides of a sequence selected from the group of complementary sequence of SEQ ID NO: 1, SEQ ID NO: 3, SEQ ID NO: 5, wherein the 3' end of said primer is located at, or at most 10, 9, 8, 7, 6, 5, 4, 3, 2 or 1 nucleotide(s) upstream of the location of the del3ins8 mutation.

In other terms, the 3' end of said primer is located at, or at most 10, 9, 8, 7, 6, 5, 4, 3, 2 or 1 nucleotide(s) upstream of, a nucleotide position selected from the group consisting of nucleotide position 1445 of SEQ ID NO: 1 or SEQ ID NO: 3, nucleotide position 1447 of SEQ ID NO:1, nucleotide position 1452 of SEQ ID NO: 3, and nucleotide positions complementary thereto. For the sake of completeness, when the sequence of SEQ ID NO: 5 is used as a reference, the 3' end of said primer is located at, or at most 10, 9, 8, 7, 6, 5, 4, 3, 2 or 1 nucleotide(s) upstream of, nucleotide position 40 019 or nucleotide position 40 021 of SEQ ID NO: 5, and nucleotide positions complementary thereto.

Therefore, the invention is directed to an isolated primer comprising:
  a contiguous span of at least 18 nucleotides of a sequence selected from the group of SEQ ID NO: 1, SEQ ID NO: 3, SEQ ID NO: 5, wherein the 3' end of said primer is located at, or at most 10 nucleotides upstream of, a nucleotide position selected from the group consisting of nucleotide position 1445 of SEQ ID NO: 1 or SEQ ID NO: 3, nucleotide position 1447 of SEQ ID NO:1, nucleotide position 1452 of SEQ ID NO: 3; or
  a contiguous span of at least 18 nucleotides of a sequence selected from the group of complementary sequence of SEQ ID NO: 1, SEQ ID NO: 3, SEQ ID NO: 5, wherein the 3' end of said primer is located at, or at most 10, 9, 8, 7, 6, 5, 4, 3, 2 or 1 nucleotide(s) upstream of and nucleotide positions complementary to nucleotide position 1445 of SEQ ID NO: 1 or SEQ ID NO: 3, nucleotide position 1447 of SEQ ID NO:1, nucleotide position 1452 of SEQ ID NO: 3.

Still another preferred embodiment of the invention is directed to a pair of primers suitable for amplifying the del3ins8 mutation comprising or consisting of a first and a second primer, each comprising or consisting of a contiguous span of at least 12 nucleotides of a sequence selected from the group of SEQ ID NO: 1, SEQ ID NO: 3, SEQ ID NO: 5 and sequences complementary thereto, wherein:
   a) said first primer hybridizes to a first DNA strand of the PNPLA1 gene;
   b) said second primer hybridizes to the strand complementary to said first DNA strand of the PNPLA1 gene; and
   c) the 3' ends of said first and second primers are located within 1000, 500, 250, 100 or 50 nucleotides of the location of the del3ins8 mutation. In other terms, the 3' ends of said first and second primers are located within 1000, 500, 250, 100 or 50 nucleotides of nucleotides positions 1445 to 1447 of SEQ ID NO: 1, of nucleotides positions 1445 to 1452 of SEQ ID NO: 3, or of nucleotide positions complementary thereto. For the sake of completeness, when the sequence of SEQ ID NO: 5 is used as a reference, the 3' ends of said first and second primers are located within 1000, 500, 250, 100 or 50 nucleotides of nucleotide positions 40019 to 40021 of SEQ ID NO: 5, or of nucleotide positions complementary thereto.

Examples of pairs of primers according to the invention are provided in Example 1, and include the pairs of primers of SEQ ID Nos. 26 and 27, SEQ ID Nos. 43 and 44, SEQ ID Nos. 45 and 46, and SEQ ID Nos. 47 and 48, which allow detecting the presence or the absence of the del3ins8 mutation.

The polynucleotides, the probes, the primers and the pairs of primers according to the invention can be used in the methods of diagnosing and/or predicting a skin disease or a metabolic disease described herein, and/or in the methods for identifying a subject which is healthy carrier or a healthy non-carrier of such a disease.

A genetic variation in the PNPLA1 gene can not only be detected at the DNA or RNA level, but also at the protein level, for example using an antibody specifically binding to the mutated PNPLA1 protein.

Thus the invention provides an isolated antibody specifically binding to a PNPLA1 polypeptide according to the invention, and to the use of such an antibody for diagnosing and/or predicting a skin disease or a metabolic disease in a subject, and/or for identifying a subject which is a healthy carrier or a healthy non-carrier of such a disease.

As used herein, the term "specifically binding" has its common meaning in the art. More specifically, an antibody specifically binds to a PNPLA1 protein if the antibody is displaced by other competitive ligands specific for the PNPLA1 protein.

In a preferred embodiment, the antibody according to the invention does not bind, or bind with a significantly lower affinity, to the PNPLA1 polypeptide shown in REFSEQ accession n° XP_538884 (30, Aug. 2005).

In a most preferred embodiment, the antibody according to the invention:
   specifically binds to a wild-type PNPLA1 polypeptide of SEQ ID NO: 2, but does not bind, or bind with a significantly lower affinity, to a PNPLA1 polypeptide of SEQ ID NO: 4 comprising the del3ins8 mutation; or
   specifically binds to a PNPLA1 polypeptide of SEQ ID NO: 4 comprising the del3ins8 mutation, but does not bind, or bind with a significantly lower affinity, to a wild-type PNPLA1 polypeptide of SEQ ID NO: 2.

The above antibodies according to the invention may be polyclonal or monoclonal. The monoclonal antibodies may be obtained from hybridomas or correspond to recombinant antibodies (e.g. chimeric, humanized or fully dog or human antibodies). The antibodies according to the invention may further be labelled in order to allow their detection.

Arrays and Kits

The present invention also relates to an array for diagnosing and/or predicting a skin disease or a metabolic disease in a subject and/or for identifying a dog which is a healthy carrier or a healthy non-carrier of such a disease, wherein said array comprises polynucleotides and/or probes as defined above.

As used herein, the term "array" refers to a set of genes, fragment of genes, oligonucleotides deposited on a support (glass slide, nylon membrane . . . ) with a high density. Numerous scientific publications about the preparation and the use of arrays are available.

In a particular embodiment, the polynucleotides and/or probes as defined above are assembled on a same solid support, preferably a standardized support. Its size can vary according to the apparatuses used to detect the presence or absence of a genetic variation as defined above.

Advantageously, the combination of polynucleotides and/or probes according to the invention is in form of a DNA matrix, comprising a support on which probes likely to hybridize to target sequences are deposed, preferably in a standardized way. The size of such supports varies according to the preparation and detection methods used. Such small supports are also referred to array.

The present invention further relates to a kit for diagnosing and/or predicting a skin disease or a metabolic disease in a subject, and/or for identifying a subject which is a healthy carrier or a healthy non-carrier of such a disease, wherein said kit comprises means for detecting a genetic variation in the PNPLA1 gene sequence.

Means for detecting a genetic variation in a gene sequence include the polynucleotides, primers, probes and antibodies described herein. Such means can be labeled with detectable compound such as fluorophores or radioactive compounds. For example, the probe or the antibody may be labeled with a detectable compound. Alternatively, when the kit comprises a antibody, the kit may further comprise a secondary antibody, labeled with a detectable compound, which binds to an unlabelled antibody specifically binding to the PNPLA1 protein.

The means for detecting a genetic variation in the PNPLA1 gene sequence may also include reagents such as e.g. reaction buffers, hybridization buffers, washing buffers and/or enzymes. The means may be present, e.g., in vials or microtiter plates, or be attached to a solid support such as a microarray as can be the case for primers and probes.

The kit may further comprise instructions regarding the diagnosis of a skin disease and/or a metabolic disease.

In a preferred embodiment, the arrays and kits according to the invention allow detecting the del3ins8 mutation in a dog.

Genotyping

The present invention further relates to a method for genotyping a dog comprising or consisting of the steps of:
   a) obtaining or providing an isolated polynucleotide from a biological sample derived from said dog; and
   b) detecting whether the genome of said dog comprises a del3ins8 allele.

The term "genotyping" a dog involves determining the specific allele or the specific nucleotide(s) carried by the dog.

Preferably, said biological sample is derived from a single individual. It is preferred that the presence of a del3ins8 allele is detected for both copies of said the PNPLA1 gene present in the individual's genome.

Any well-known method of genotyping may be used in the frame of the present invention. Such methods include methods such as e.g. conventional dot blot analyzes, single strand conformational polymorphism analysis, denaturing gradient gel electrophoresis, heteroduplex analysis and mismatch cleavage detection. Another method for determining the identity of the nucleotide present at a particular polymorphic site employs a specialized exonuclease-resistant nucleotide derivative as described in U.S. Pat. No. 4,656,127. Oligonucleotide microarrays or solid-phase capturable dideoxynucleotides and mass spectrometry may also be used. Preferred methods involve directly determining the identity of the nucleotide present at an allelic marker site by sequencing assay, enzyme-based mismatch detection assay, or hybridization assay.

In a preferred embodiment, the method of genotyping of the invention further comprises the step of correlating the result of the genotyping steps with a risk of suffering from a skin disease or a metabolic disease.

Therapeutic Uses

It has been found that dogs bearing two copies of the del3ins8 allele, which leads to the synthesis of a truncated PNPLA1 polypeptide of only 491 amino acids, suffers from or are at risk of suffering from ichthyosis. Therefore, the absence of a functional PNPLA1 protein is believed to cause skin diseases. In addition, the inventors came to the conclusion that the absence of a functional PNPLA1 protein or an alteration of its biological activity may be involved in the development of metabolic diseases as well.

The invention thus pertains to an isolated wild-type PNPLA1 polypeptide for use as a medicament, and to pharmaceutical compositions comprising or consisting of a wild-type polypeptide and a physiologically acceptable carrier.

More specifically, the invention pertains to an isolated wild-type PNPLA1 polypeptide for use in the treatment or prevention of a skin disease or a metabolic disease in a subject, and to methods for treating and/or preventing a skin disease or a metabolic disease comprising or consisting of the step of administering an effective amount of a wild-type PNPLA1 polypeptide to a subject in need thereof.

By "wild-type PNPLA1 polypeptide" is meant a PNPLA1 polypeptide having biological activity. The biological activity of the PNPLA1 polypeptide is defined herein as being the ability to avoid excessive scaling of the skin. This biological activity is believed to be linked with the lipid hydrolase activity of the PNPLA1 protein. In addition, the region extending from position 480 to position 522 of SEQ ID NO: 2 appears to be crucial for the biological activity of the PNPLA1 protein.

When a dog is to be treated, a wild-type PNPLA1 polypeptide of SEQ ID NO: 2 may for example be used. When a human being is to be treated, isoform 1 shown in Swiss-Prot accession n° Q8N8W4 (last modified Sep. 1, 2009. Version 49) may for example be used. Alternatively, derivatives thereof may also be used provided that:
- the derivative is capable of inhibiting and/or reducing scaling of the skin; and/or
- the derivative exhibits lipid hydrolase activity; and/or
- the sequence of the derivative comprises the region extending from position 480 to position 522 of SEQ ID NO: 2 (corresponding to amino acids 490 to 532 of isoform 1 of the human PNPLA1 protein shown in Swiss-Prot accession n° Q8N8W4).

The term "derivative" includes fragments, homologues, mutants and naturally-occurring variants such as allelic variants, splice variants or variants obtained through proteolytic processing. Derivatives may comprise mutations such as deletions, insertions and/or substitutions compared to the reference sequence. In case of substitutions, the substitution may correspond to a conservative substitution as indicated in the table below.

By "treatment" is meant a therapeutic use (i.e. on a patient having a given disease) and by "preventing" is meant a prophylactic use (i.e. on an individual susceptible of developing a given disease). The term "treatment" not only includes treatment leading to complete cure of the diseases, but also treatments slowing down the progression of the disease.

By "effective amount" is meant an amount sufficient to achieve a concentration of peptide which is capable of preventing, treating or slowing down the disease to be treated. Such concentrations can be routinely determined by those of skilled in the art. The amount of the compound actually administered will typically be determined by a physician or a veterinarian, in the light of the relevant circumstances, including the condition to be treated, the chosen route of administration, the actual compound administered, the age, weight, and response of the subject, the severity of the subject's symptoms, and the like. It will also be appreciated by those of skilled in the art that the dosage may be dependent on the stability of the administered peptide.

By "subject in need thereof" is meant an individual suffering from or susceptible of suffering from the skin disease to be treated or prevented. The individuals to be treated in the frame of the invention are preferably human beings or dogs.

The invention also contemplates the use of a polynucleotide encoding a wild-type PNPLA1 polypeptide in the frame of e.g. a treatment of a skin disease or a metabolic disease by gene therapy. In this case, the polynucleotide is preferably present on an expression vector, on which the sequence coding for the peptide is placed under the control of expression signals (e.g. a promoter, a terminator and/or an enhancer) allowing its expression. The expression vector may for example correspond to a viral vector such as an adenoviral or a lentiviral vector.

All references cited herein, including journal articles or abstracts, published patent applications, issued patents or any other references, are entirely incorporated by reference herein, including all data, tables, figures and text presented in the cited references.

The invention will be further evaluated in view of the following examples and figures.

BRIEF DESCRIPTION OF THE FIGURES

FIG. 1 represents a sequence alignment between the wild-type allele and the del3ins8 allele of dog PNPLA1 protein or cDNA. A. Polynucleotide alignment between nucleotides 1416 to 1480 of SEQ ID NO: 1 (wild-type allele of dog PNPLA1) and nucleotides 1416 to 1485 of SEQ ID NO: 3 (del3ins8 allele of dog PNPLA1). B. Polypeptide alignment between the C-terminal extremities of the del3ins8 and wild-type alleles, i.e. between amino acids 451 to 565 of SEQ ID NO: 2 (wild-type allele of dog PNPLA1) and amino acids 451 to 491 of SEQ ID NO: 4 (del3ins8 allele of dog PNPLA1). The box indicates a conserved region between PNPLA1 proteins from *Canis familiaris*, *Homo sapiens*, *Pan troglodytes*, *Bos Taurus*, *Equus caballis*, *Mus musculus* and *Rattus norvegicus*.

BRIEF DESCRIPTION OF THE SEQUENCES

Figure 2:
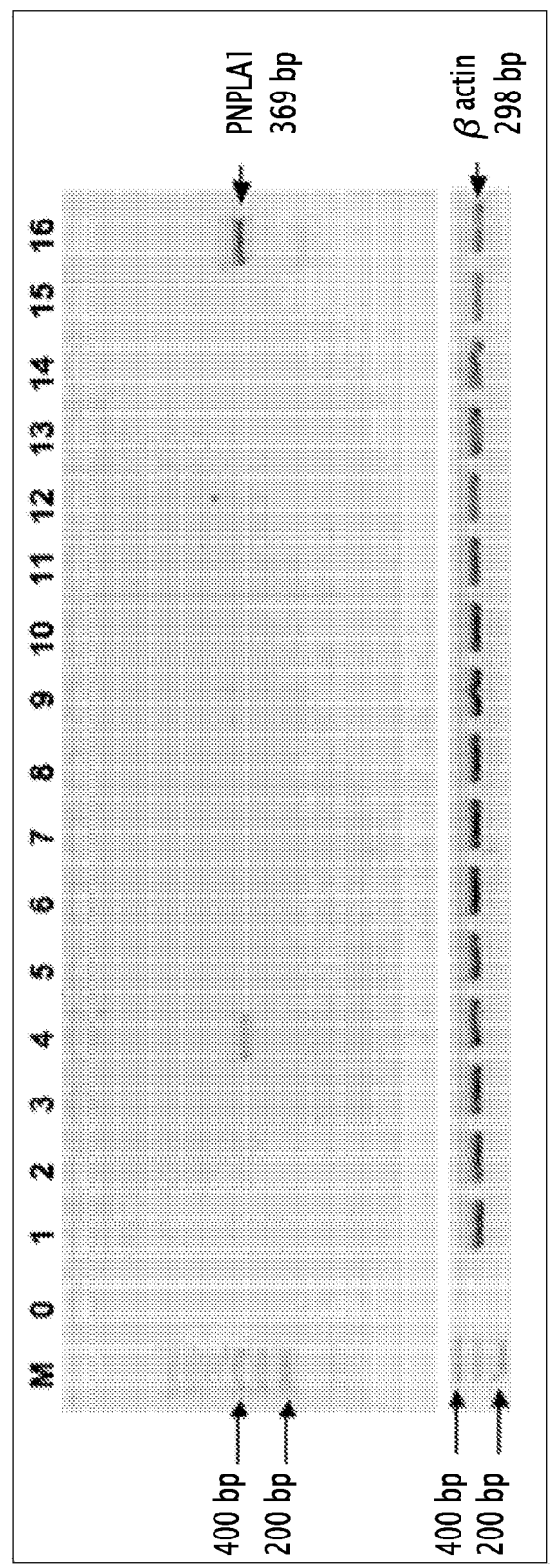
FIG. 2 represents the distribution of wild-type PNPLA1 mRNA expression in dog tissues. β-actin is used as a control. 1: pituitary gland, 2: spinal cord, 3: cerebellum, 4: occipital lobe, 5: heart, 6: stomach, 7: lymph node, 8: small intestine, 9: colon, 10: kidney, 11: pancreas. 12: thyroid, 13: lung, 14: spleen, 15: liver, 16: skin.

SEQ ID NO: 1 represents the coding sequence of the wild-type allele of dog PNPLA1 cDNA expressed in skin.

SEQ ID NO: 2 represents the polypeptide encoded by SEQ ID NO: 1.

SEQ ID NO: 3 represents the coding sequence of the del3ins8 mutant allele of dog PNPLA1 cDNA.

SEQ ID NO: 4 represents the polypeptide encoded by SEQ ID NO: 3.

SEQ ID NO: 5 represents the dog PNPLA1 gene.

SEQ ID Nos. 6-50 represent primers.

EXAMPLES

Example 1

Materials and Methods 1.1. Pedigree Collection

The pedigree of 108 dogs was constructed using clinical and genealogical data from veterinarians, breeders and owners, with the Cyrillic software v2.1 (CyrillicSoftware, United Kingdom) which manages genealogic and genetic data.

1.2. Tissue and Blood Sampling

Blood and tissue samples, together with the pedigrees of the dogs (when possible), were collected by a network including the French National Veterinary Schools, the Liege Veterinary School, pathology laboratories and licensed veterinarians from France. All data were entered into a canine bio-bank hosted at the CNRS in Rennes. All affected dogs had clinical evidence of ichthyosis and in most of the cases, the disease was confirmed by pathology reports made on samples of skin punch biopsy. Unaffected dogs were declared as controls if they were older than 3 years old and if they did not show any scaling on the skin.

1.3. RNA and DNA Isolation

Genomic DNA was extracted from peripheral blood leucocytes (5 mL of blood in EDTA tubes) using the Nucleospin blood kit (Macherey Nagel, Germany) according to the manufacturer's instructions. Tissue biopsy samples were stored in RNAlater (Quiagen, The Netherlands) at −20° C., and RNA was extracted from tissues using the Nucleospin RNA kit (Macherey Nagel, Germany) according to the manufacturer's instructions.

1.4. Genotyping and Genetic Analysis

Genotype data were generated on the "v2 platinum" canine SNP Affymetrix chip for 49 658 SNPs at the Centre National de Génotypage (CNG, Paris, France). Genotypes were analyzed and p-values were calculated using the Plink software.

1.5. Locus Identification and Exon Sequencing

Sequencing was carried out using the BigDye® Terminator v1.1 or v3.1 Cycle Sequencing Kit (Applied Biosystems, USA) according to the manufacturer's instructions. Products of this reaction were purified on Sephadex G-50 gel (GE Healthcare, USA). DNA sequencing was made by capillary electrophoresis with the 3130xl Genetic Analyzer (Applied Biosystems, USA). Sequence data were aligned using SeqScape Software v2.5 (Applied Biosystems, USA).

1.6. Analysis of the Sequences

Reverse transcription (RT) of total RNA from tissue biopsy samples was performed using the high-capacity cDNA Archive kit (Applied Biosystems, USA). Primers sets were designed using the Primer 3 program (available at the frodo.wi.mit.edu/primer3 website) based on canine PNPLA1 sequence data available from the following database entries: NCBI accession No. NC_006594.2, NCBI accession No. XM_538884.2, Ensembl accession No. ENSCAFG00000001392, and accession No. ENSCAFT00000002155. All exons, including exon-intron junctions, of canine PNPLA1 gene and junctions in the cDNA were amplified. For amplification, touch-down PCR reactions were carried out with the AmpliTaq Gold polymerase (Applied Biosystems, USA) in a 10 µL sample containing 10 ng of genomic DNA. The initial hybridization step was performed at 61° C. followed by 15 cycles in which the hybridization temperature was reduced by 0.5° C. each cycle to reach the final temperature of 51° C. The 30 next cycles were performed at an hybridization temperature of 51° C. 3 µL of PCR products were resolved with Bromophenol Blue by electrophoresis through a 2.0% agarose gels containing 25 µg/mL of BET. 2 µL of PCR products were purified with ExoSAP-IT (GE Healthcare, USA) according to the manufacturer's instructions. Sequencing reaction was performed using the BigDye® Terminator v1.1 or v3.1 Cycle Sequencing Kit (Applied Biosystems, USA) according to the manufacturer's instructions. Products of this reaction were purified on a Sephadex G-50 gel (GE Healthcare, USA). DNA sequencing was made by capillary electrophoresis with the 3130xl Genetic Analyzer (Applied Biosystems, USA). Sequence data were aligned using SeqScape Software v2.5 (Applied Biosystems, USA).

Screening for mutations in PNPLA1 was performed on genomic DNA by PCR amplification, followed by sequencing.

1.7. RNA Expression Analysis

RNA were extracted from tissue samples using the Nucleospin RNA kit (Macherey Nagel, Germany) according to the manufacturer's instructions.

1.8. Cloning of Canine PNPLA1 cDNA was prepared using the 5' RACE method, starting from total RNA extracted from tissue biopsy samples of a healthy dog.

1.9. Primers

Table 1 shows the primers used for sequencing the exons of the genomic sequence of the PNPLA1 gene. SEQ ID Nos. 24 and 25 correspond to the primers allowing amplifying the newly identified exon 7. SEQ ID Nos. 26 and 27 correspond to the primers allowing amplifying the ins3del8 mutation.

TABLE 1

| Name | Amplicon size | SEQ ID No. of forward primer | SEQ ID No. of reverse primer | Exon in ENSEMBL annotation | Correct annotation |
|---|---|---|---|---|---|
| PNPLA1-1 | 367 | 6 | 7 | exon 1 | exon 1 |
| PNPLA1-2 | 391 | 8 | 9 | exon 2 | exon 2 |
| PNPLA1-3 | 230 | 10 | 11 | exon 3 | exon 3 |
| PNPLA1-4 | 398 | 12 | 13 | exon 4 | exon 4 |
| PNPLA1-5 | 250 | 14 | 15 | exon 5 | exon 5 |
| PNPLA1-6a | 498 | 16 | 17 | exon 6 | exon 6 |
| PNPLA1-6b | 399 | 18 | 19 | exon 6 | exon 6 |
| PNPLA1-7 | 248 | 20 | 21 | exon 7 | n/a |
| PNPLA1-8 | 200 | 22 | 23 | exon 8 | n/a |
| PNPLA1-7bis | 250 | 24 | 25 | n/a | exon 7 |
| PNPLA1-9 | 300 | 26 | 27 | exon 9 | exon 8 |
| PNPLA1-10 | 287 | 28 | 29 | exon 10 | exon 9 |
| PNPLA1-11 | 242 | 30 | 31 | exon 11 | exon 10 |

Table 2 shows the primers used for amplifying and/or sequencing the cDNA of PNPLA1. SEQ ID Nos. 45 and 46 were specifically designed for amplifying the del3ins8 allele. SEQ ID Nos. 47 and 48 were specifically designed for amplifying the wild-type allele.

TABLE 2

| Name | Amplicon size | SEQ ID No. of forward primer | SEQ ID No. of reverse primer | Amplified region |
|---|---|---|---|---|
| PNPLA1-ARN12 | 435 | 32 | 33 | Exons 1-2 |
| PNPLA1-ARN4 | 300 | 34 | 35 | Exons 1-2 |
| PNPLA1-ARN24 | 327 | 36 | 37 | Exons 2-4 |
| PNPLA1-ARN5 | 219 | 36 | 38 | Exons 2-4 |
| PNPLA1-ARN6 | 242 | 39 | 40 | Exons 4-6 |
| PNPLA1-ARN66 | 466 | 41 | 42 | Exon 6 |
| PNPLA1-ARN2 | 369 | 43 | 44 | Exons 6-10 |
| PNPLA1-ARNmut | 303 | 45 | 46 | |
| PNPLA1-ARNsauv | 308 | 47 | 48 | |

SEQ ID Nos. 49 and 50 correspond to the primers used for amplifying and/or sequencing the cDNA of β-actin.

Example 2

Results

Blood and tissue samples from 800 dogs, together with the accompanying pedigree when available, were collected by a network including the French National Veterinary Schools, the Liege Veterinary School, pathology laboratories and licensed veterinarians from France.

Out of 300 Golden retrievers, DNA from 40 unrelated dogs (20 affected dogs and 20 non-affected dogs) was selected for further analysis. Genomic DNA was extracted from peripheral blood leucocytes of these blood and tissue samples. Genotype data were generated using the canine SNP Affymetrix chips for 49 658 SNPs. Genotypes were analyzed and p-values were calculated using the Plink software.

It was found that a genomic region of about 9 megabases of canine chromosome 12 encompassed the best statistical p-value. An exhaustive analysis of this region revealed three candidate genes.

Samples from 24 dogs (twelve affected dogs and twelve unaffected dogs) were used for sequencing all exons of these three candidate genes.

One of these three candidate genes corresponded to the Patatin-like phospholipase domain-containing protein 1 (PNPLA1) gene. This gene is a poorly characterized gene, which belongs to the adiponutrin gene family. Proteins of the adiponutrin family are believed to have both lipolytic and lipogenic properties (Johansson et al., 2009, PLoS One. 4:e5327). The human PNPLA1 protein is annotated as being a putative lipid hydrolase (see e.g. Swiss-Prot accession n° Q8N8W4).

The sequencing of the PNPLA1 gene, carried out starting from cDNA prepared form healthy dog skin biopsies, allowed correcting the sequence of the PNPLA1 gene and of the PNPLA1 cDNA that are found in public databases (NCBI accession Nos. NC_006594.2 and XM_538884.2, Ensembl accession No. ENSCAFG00000001392 and ENSCAFT00000002155). The corrected sequence of the dog PNPLA1 gene, with corrected introns/exons boundaries corresponding to the boundaries found in the skin transcript, is shown as SEQ ID NO: 5.

A mutation referred to as del3ins8 was identified in exon 8 of the corrected PNPLA1 gene sequence. This mutation, which is shown on FIG. 1A, is a deletion of three bases combined with an insertion of 8 bases. This mutation results in a frameshift and leads to the presence of a premature stop codon in the resulting coding sequence. As a consequence, the encoded protein lacks 74 amino acids at its C-terminal extremity (FIG. 1B). This mutation is located in a region that in well conserved between PNPLA1 proteins of different organisms (FIG. 1B). Moreover, it has been shown that mutations leading to a truncation of the C-terminal extremity of the closely related PNPLA2 protein are loss of function mutations (Fischer et al. 2007 Nat Genet. 39:28-30). Therefore, the del3ins8 mutation very likely corresponds to a loss of function mutation.

In addition, as shown in SEQ ID NO: 5, there appears to exist two alternative exons 6. The first exon 6 (positions 35164 to 35748 of SEQ ID NO: 5) is predicted to lead to the synthesis of a protein of 565 amino acids (shown as SEQ ID NO: 1). The second exon 6 (positions 35164 to 35802 of SEQ ID NO: 5) is predicted to lead to the synthesis of a protein of 583 amino acids.

Total RNA was extracted from tissue biopsy samples from an unaffected dog, and PCR reactions amplifying the PNPLA1 cDNA were performed on a series of 15 tissues. It was shown that PNPLA1 is highly expressed in skin. It was also slightly expressed in brain and in colon, although at a much lesser extent. No expression was found in the 12 other studied tissues (FIG. 2).

Total RNA was further extracted from skin biopsy samples from unaffected and from affected dogs. PCR reactions amplifying the PNPLA1 cDNA were carried out. The mRNA was expressed in the skin of all dogs.

The region comprising the del3ins8 mutation was sequenced. RNAs were extracted from skin (punch biopsie) for 15 dogs. The RNAs were retrotranscribed into cDNAs. The cDNAs were either sequenced or PCR amplified with del3ins8 mutation specific primers of SEQ ID Nos 45-46 and/or 47-48.

In skin, the PNPLA1 mRNAs were found to comprise the first exon 6 (i.e. positions 35164 to 35748 of SEQ ID NO: 5), thereby leading to the synthesis of a PNPLA1 protein of SEQ ID NO: 2 or 4.

Eleven dogs were confirmed to carry the del3ins8 mutation at the homozygous state. Two dogs were heterozygous. Two dogs were homozygous for the wild-type allele. Sequencing showed the presence of a homozygous mutated sequence in RNA extracted from tissues of affected dogs. Unaffected dogs were either homozygous for the normal sequence (healthy non-carriers dogs) or heterozygous (healthy carriers). This experiment thus confirmed that the mutation is found in the cDNA obtained from skin RNAs with a perfect concordance between the phenotype and the mutational status of the DNA and RNA.

In summary, it has been found that:
  Golden Retrievers suffering from ichthyosis displayed the del3ins8 mutation in both alleles of the PNPLA1 gene, whereas healthy Golden Retrievers displayed either two wild-type alleles of the PNPLA1 gene, or one wild-type allele together with one mutated allele;
  The del3ins8 mutation results in the synthesis of a PNPLA1 protein lacking 74 amino acids at its C-terminal extremity. The del3ins8 mutation very likely corresponds to a loss of function mutation; and
  PNPLA1 is specifically expressed at high levels in the skin.
  Taken together, these results show that PNPLA1 is the gene that causes ichthyosis in Golden Retrievers.

This finding is further corroborated by the fact that the PNPLA1 protein is annotated as being a lipid hydrolase (see e.g. Swiss-Prot accession n° Q8N8W4), and that in human beings, many types of ichthyoses correspond to disorders of the lipid metabolism (Elias et al. 2008 J Lipid Res. 49:697-714). Moreover, CGI58 has been discovered mutated in human subjects affected with ichthyosis in the frame of the Dorfmann-Chanarin syndrome (Caux et al., 2004 Am J Med Genet A. 129A:214; Ben Selma et al., 2007 J Invest Dermatol. 127:2273-6). CGI58 positively regulates PNPLA2, a PNPLA1 paralog.

Further, since PNPLA1 gene is almost exclusively expressed in the epidermis of the skin, more particularly in the keratinocytes, it is likely that lack of expression of PNPLA1, or expression of a non-functional PNPLA1, also triggers cornification disorders different from ichthyoses.

In addition, the facts that:

PNPLA1 belongs to the PNPLA family ("Patatin like phospholipase domain containing proteins" family), the members of which present a lipid hydrolase activity with different substrate specificities (Kienesberger et al., J Lipid Res. 2009; 50 Suppl:S63-8);

PNPLA1 is slightly expressed in intestine; and

Golden Retrievers, among which the del3ins8 mutation is very wide-spread, have a higher risk of becoming obese than many other dog breeds;

further suggest that PNPLA1 may be involved in the development of metabolic diseases.

The invention claimed is:

1. cDNA comprising a sequence selected from the group consisting of:
   a) the sequence at least 93% identical to the sequence of SEQ ID NO: 1, wherein said cDNA comprises nucleotides 1445 to 1447 of SEQ ID NO: 1;
   b) the sequence at least 80% identical to the sequence of SEQ ID NO: 3, wherein said cDNA comprises nucleotides 1444 to 1452 of SEQ ID NO: 3; and
   c) the sequence complementary to the sequence of (a) or (b).

2. An isolated probe comprising a contiguous span of at least 18 nucleotides of a sequence selected from the group of SEQ ID NO: 1, SEQ ID NO: 3, SEQ ID NO: 5 and sequences complementary thereto, wherein said contiguous span comprises nucleotide positions 1445 to 1447 of SEQ ID NO: 1, nucleotide positions 1445 to 1452 of SEQ ID NO: 3, nucleotide positions 40019 to 40021 of SEQ ID NO: 5, or nucleotide positions complementary thereto, wherein said probe is labelled with a detectable moiety, wherein the detectable moiety is not a nucleotide sequence.

3. An array comprising at least one probe as defined in claim 2.

4. An isolated primer comprising:
   a contiguous span of at least 18 nucleotides of a sequence selected from the group of SEQ ID NO: 1, SEQ ID NO: 3, SEQ ID NO: 5, wherein the 3' end of said primer is located at, or at most 10 nucleotides upstream of, a nucleotide position selected from the group consisting of nucleotide position 1445 of SEQ ID NO: 1 or SEQ ID NO: 3, nucleotide position 1447 of SEQ ID NO:1, nucleotide position 1452 of SEQ ID NO: 3, and nucleotide position 40019 of SEQ ID NO: 5; or a contiguous span of at least 18 nucleotides of a sequence selected from the group of sequences complementary to of SEQ ID NO: 1, SEQ ID NO: 3 or SEQ ID NO: 5, wherein the 3' end of said primer is located at, or at most 10 nucleotides upstream of, a nucleotide position complementary to nucleotide position 1445 of SEQ ID NO: 1 or SEQ ID NO: 3, nucleotide position 1447 of SEQ ID NO:1, nucleotide position 1452 of SEQ ID NO: 3, and nucleotide position 40019 of SEQ ID NO: 5, wherein said primer is labelled with a detectable moiety, wherein the detectable moiety is not a nucleotide sequence.

5. A kit for diagnosing and/or predicting a cornification disorder in a dog, and/or for identifying a dog which is a healthy carrier or a healthy non-carrier of said cornification disorder, wherein said kit comprises at least one means for detecting a genetic variation in the PNPLA1 gene sequence selected from the group consisting of a probe as defined in claim 2, an array as defined in claim 3, and a primer as defined in claim 4, wherein said genetic variation consists of a replacement of nucleotides 1445 to 1447 of SEQ ID NO: 1 with eight nucleotides consisting of TACTACTA.

6. An isolated probe comprising a contiguous span of at least 18 nucleotides of the sequence selected from the group consisting of SEQ ID NO: 1, SEQ ID NO: 3, SEQ ID NO: 5 and the sequences complementary thereto, wherein said contiguous span comprises nucleotide positions 1445 to 1447 of SEQ ID NO: 1, nucleotide positions 1445 to 1452 of SEQ ID NO: 3, nucleotide positions 40019 to 40021 of SEQ ID NO: 5, or nucleotide positions complementary thereto, wherein said probe is labelled with a detectable moiety, wherein the detectable moiety is a moiety capable of generating a radioactive signal, a calorimetric signal, a fluorescent signal, a chemiluminescent signal or a electrochemiluminescent signal.

7. An array comprising at least one probe as defined in claim 6.

8. An isolated primer comprising:
a contiguous span of at least 18 nucleotides of the sequence selected from the group consisting of SEQ ID NO: 1, SEQ ID NO: 3 and SEQ ID NO: 5, wherein the 3' end of said primer is located at, or at most 10 nucleotides upstream of, a nucleotide position selected from the group consisting of nucleotide position 1445 of SEQ ID NO: 1 or SEQ ID NO: 3, nucleotide position 1447 of SEQ ID NO:1, nucleotide position 1452 of SEQ ID NO: 3, and nucleotide position 40019 of SEQ ID NO: 5; or
a contiguous span of at least 18 nucleotides of the sequence complementary to the group consisting of SEQ ID NO: 1, SEQ ID NO: 3 and SEQ ID NO: 5, wherein the 3' end of said primer is located at, or at most 10 nucleotides upstream of, a nucleotide position complementary to nucleotide position 1445 of SEQ ID NO: 1 or SEQ ID NO: 3, nucleotide position 1447 of SEQ ID NO:1, nucleotide position 1452 of SEQ ID NO: 3, and nucleotide position 40019 of SEQ ID NO: 5, wherein said primer is labelled with a detectable moiety, wherein the detectable moiety is a moiety capable of generating a radioactive signal, a calorimetric signal, a fluorescent signal, a chemiluminescent signal or a electrochemiluminescent signal.

* * * * *

SEQUENCE LISTING

```
<160> NUMBER OF SEQ ID NOS: 50

<210> SEQ ID NO 1
<211> LENGTH: 1698
<212> TYPE: DNA
<213> ORGANISM: Canis familiaris
<220> FEATURE:
<221> NAME/KEY: CDS
<222> LOCATION: (1)..(1698)

<400> SEQUENCE: 1 atg gaa gag cag gtg ttc aag ggg gac cca gac act ccc cat tcc atc      48
Met Glu Glu Gln Val Phe Lys Gly Asp Pro Asp Thr Pro His Ser Ile
1               5                   10                  15 tcc ttc tcc ggc agt gga ttt ctc tcc ttc tac cag gcc ggg gct gtg      96
Ser Phe Ser Gly Ser Gly Phe Leu Ser Phe Tyr Gln Ala Gly Ala Val
                20                  25                  30 gat gcc ctt cga gac ttg gcc ccc cgg atg ctg gaa acg gcc cac cgc     144
Asp Ala Leu Arg Asp Leu Ala Pro Arg Met Leu Glu Thr Ala His Arg
            35                  40                  45 ttt gcc ggg aca tca gca ggt gca gtg gtg gcg gct ctg gtc atc tgt     192
Phe Ala Gly Thr Ser Ala Gly Ala Val Val Ala Ala Leu Val Ile Cys
        50                  55                  60 ggg att gaa atg gat gag tac ctg aga gtc ctc aat gta ggt gtg gct     240
Gly Ile Glu Met Asp Glu Tyr Leu Arg Val Leu Asn Val Gly Val Ala
65                  70                  75                  80 gag gtg aag aaa tcc ttc ctg ggg ccc ttg tcg cca tcg tgc aag atg     288
Glu Val Lys Lys Ser Phe Leu Gly Pro Leu Ser Pro Ser Cys Lys Met
                85                  90                  95 gtg cag ctg atg cgg cag ttt ctg tat agg gtc ctg ccc gag gac tcc     336
Val Gln Leu Met Arg Gln Phe Leu Tyr Arg Val Leu Pro Glu Asp Ser
                100                 105                 110 tac aag gtc gcc aca ggg aag ctc cac gtg tcc ctc act cgg ctc acg     384
Tyr Lys Val Ala Thr Gly Lys Leu His Val Ser Leu Thr Arg Leu Thr
            115                 120                 125 gac gga gag agt gtc gtg gtt tca gag tat aca tcc aag gaa gag ctc     432
Asp Gly Glu Ser Val Val Val Ser Glu Tyr Thr Ser Lys Glu Glu Leu
        130                 135                 140 atc gag gca ctg tac tgc agc tgc ttt gtc ccc gtg tac tgt gga ctc     480
Ile Glu Ala Leu Tyr Cys Ser Cys Phe Val Pro Val Tyr Cys Gly Leu
145                 150                 155                 160 atc ccc cca act tac cgt ggt gtg cgc tac att gac ggg ggc ttc acg     528
Ile Pro Pro Thr Tyr Arg Gly Val Arg Tyr Ile Asp Gly Gly Phe Thr
                165                 170                 175 ggc atg cag ccc tgc tcc ttc tgg acc gac tcc att acc atc tcc acc     576
Gly Met Gln Pro Cys Ser Phe Trp Thr Asp Ser Ile Thr Ile Ser Thr
                180                 185                 190 ttc agc ggg cag caa gac atc tgt ccc cgg gac tgc ccc gcc atc ttc     624
Phe Ser Gly Gln Gln Asp Ile Cys Pro Arg Asp Cys Pro Ala Ile Phe
```

-continued

```
              195                 200                 205
cac gac ttc cgc atg ttc aac tgc tcc ttc cag ttc tcc ctg gaa aac      672
His Asp Phe Arg Met Phe Asn Cys Ser Phe Gln Phe Ser Leu Glu Asn
    210                 215                 220 atc gcc agg atg acc cat gcc ctg ttc ccg cca gac cta ttg atc ctg      720
Ile Ala Arg Met Thr His Ala Leu Phe Pro Pro Asp Leu Leu Ile Leu
225                 230                 235                 240 cac aac tac tac tac cga ggg tat gaa gat gct gtt tca tac ttg agg      768
His Asn Tyr Tyr Tyr Arg Gly Tyr Glu Asp Ala Val Ser Tyr Leu Arg
                245                 250                 255 cgg ctg aat gct gct tac atc aat tct ccc tcc aag aga gtg ata ttc      816
Arg Leu Asn Ala Ala Tyr Ile Asn Ser Pro Ser Lys Arg Val Ile Phe
            260                 265                 270 ccc cgt gta gaa gtg tac tgc aat ata gaa ctt gcc ctt ggc aac gag      864
Pro Arg Val Glu Val Tyr Cys Asn Ile Glu Leu Ala Leu Gly Asn Glu
        275                 280                 285 tgc cac gaa tgc agt cag tca agc ctc caa aca cag cag caa gaa tcc      912
Cys His Glu Cys Ser Gln Ser Ser Leu Gln Thr Gln Gln Gln Glu Ser
    290                 295                 300 ata caa ctt cac aca cag agg gct cct gaa gga gaa gga aag ggc agc      960
Ile Gln Leu His Thr Gln Arg Ala Pro Glu Gly Glu Gly Lys Gly Ser
305                 310                 315                 320 cac ggt tca ctt ccg tcc tca cct gtg cag aca ccc gga gcc aca tgt     1008
His Gly Ser Leu Pro Ser Ser Pro Val Gln Thr Pro Gly Ala Thr Cys
                325                 330                 335 gag tgg cct gta gag tca cct gtt tca cca cct gtc cct tca ctt gag     1056
Glu Trp Pro Val Glu Ser Pro Val Ser Pro Pro Val Pro Ser Leu Glu
            340                 345                 350 cag tca cct gca act cca ctg gct tca tca cca tca cat tct gca gct     1104
Gln Ser Pro Ala Thr Pro Leu Ala Ser Ser Pro Ser His Ser Ala Ala
        355                 360                 365 gac ctg ccc cct gct tcg ctc cca gct gta ccc tta cca ctc agc tca     1152
Asp Leu Pro Pro Ala Ser Leu Pro Ala Val Pro Leu Pro Leu Ser Ser
    370                 375                 380 aca ctt gag ctg tca cgt gta tca cca cag cag cag gta caa act act     1200
Thr Leu Glu Leu Ser Arg Val Ser Pro Gln Gln Gln Val Gln Thr Thr
385                 390                 395                 400 gga tcg cca cca aga tcc cca cct tcc cag tca tct ctg tca cac agg     1248
Gly Ser Pro Pro Arg Ser Pro Pro Ser Gln Ser Ser Leu Ser His Arg
                405                 410                 415 cca ccc ttg ggg cct tca tct gta ggg gca tct caa aca ctg ccc caa     1296
Pro Pro Leu Gly Pro Ser Ser Val Gly Ala Ser Gln Thr Leu Pro Gln
            420                 425                 430 cgt tct tct tca gca tca cct gca cag cca cct gtg gag gaa cta ggc     1344
Arg Ser Ser Ser Ala Ser Pro Ala Gln Pro Pro Val Glu Glu Leu Gly
        435                 440                 445 cca gaa cag tcc caa gct ccc ctt gcc tct tca aag cca gaa ggt acc     1392
Pro Glu Gln Ser Gln Ala Pro Leu Ala Ser Ser Lys Pro Glu Gly Thr
    450                 455                 460 aca cct ttg gtt aat gtg aag gaa gcc acc agc aag cct cat gca atg     1440
Thr Pro Leu Val Asn Val Lys Glu Ala Thr Ser Lys Pro His Ala Met
465                 470                 475                 480 gga aac cct act gaa gac tcc agt tgg atg agc aag gtg ttc aag aag     1488
Gly Asn Pro Thr Glu Asp Ser Ser Trp Met Ser Lys Val Phe Lys Lys
                485                 490                 495 aac aaa caa aag aca agt agc acc aga aaa ggc ttc cca aga cac cca     1536
Asn Lys Gln Lys Thr Ser Ser Thr Arg Lys Gly Phe Pro Arg His Pro
            500                 505                 510 cga tcc aaa aaa aca ggc ggc aaa gtg cag tct gct ccc tgt ccc ctc     1584
```

```
Arg Ser Lys Lys Thr Gly Gly Lys Val Gln Ser Ala Pro Cys Pro Leu
            515                 520                 525 gac ttc act ctg ctc tcc act tcc gag aca gtt tgg gtc acc tac agg      1632
Asp Phe Thr Leu Leu Ser Thr Ser Glu Thr Val Trp Val Thr Tyr Arg
530                 535                 540 cct cat ccc agc cag atc cag gaa cac agc tgt cct gag gaa gct gtg      1680
Pro His Pro Ser Gln Ile Gln Glu His Ser Cys Pro Glu Glu Ala Val
545                 550                 555                 560 aac caa gag aga act tga                                              1698
Asn Gln Glu Arg Thr
                565

<210> SEQ ID NO 2
<211> LENGTH: 565
<212> TYPE: PRT
<213> ORGANISM: Canis familiaris

<400> SEQUENCE: 2

Met Glu Glu Gln Val Phe Lys Gly Asp Pro Asp Thr Pro His Ser Ile
1               5                   10                  15

Ser Phe Ser Gly Ser Gly Phe Leu Ser Phe Tyr Gln Ala Gly Ala Val
            20                  25                  30

Asp Ala Leu Arg Asp Leu Ala Pro Arg Met Leu Glu Thr Ala His Arg
        35                  40                  45

Phe Ala Gly Thr Ser Ala Gly Ala Val Val Ala Leu Val Ile Cys
    50                  55                  60

Gly Ile Glu Met Asp Glu Tyr Leu Arg Val Leu Asn Val Gly Val Ala
65                  70                  75                  80

Glu Val Lys Lys Ser Phe Leu Gly Pro Leu Ser Pro Ser Cys Lys Met
                85                  90                  95

Val Gln Leu Met Arg Gln Phe Leu Tyr Arg Val Leu Pro Glu Asp Ser
            100                 105                 110

Tyr Lys Val Ala Thr Gly Lys Leu His Val Ser Leu Thr Arg Leu Thr
        115                 120                 125

Asp Gly Glu Ser Val Val Val Ser Glu Tyr Thr Ser Lys Glu Glu Leu
130                 135                 140

Ile Glu Ala Leu Tyr Cys Ser Cys Phe Val Pro Val Tyr Cys Gly Leu
145                 150                 155                 160

Ile Pro Pro Thr Tyr Arg Gly Val Arg Tyr Ile Asp Gly Gly Phe Thr
                165                 170                 175

Gly Met Gln Pro Cys Ser Phe Trp Thr Asp Ser Ile Thr Ile Ser Thr
            180                 185                 190

Phe Ser Gly Gln Gln Asp Ile Cys Pro Arg Asp Cys Pro Ala Ile Phe
        195                 200                 205

His Asp Phe Arg Met Phe Asn Cys Ser Phe Gln Phe Ser Leu Glu Asn
210                 215                 220

Ile Ala Arg Met Thr His Ala Leu Phe Pro Pro Asp Leu Leu Ile Leu
225                 230                 235                 240

His Asn Tyr Tyr Tyr Arg Gly Tyr Glu Asp Ala Val Ser Tyr Leu Arg
                245                 250                 255

Arg Leu Asn Ala Ala Tyr Ile Asn Ser Pro Ser Lys Arg Val Ile Phe
            260                 265                 270

Pro Arg Val Glu Val Tyr Cys Asn Ile Glu Leu Ala Leu Gly Asn Glu
        275                 280                 285

Cys His Glu Cys Ser Gln Ser Ser Leu Gln Thr Gln Gln Gln Glu Ser
290                 295                 300
```

```
Ile Gln Leu His Thr Gln Arg Ala Pro Glu Gly Glu Gly Lys Gly Ser
305                 310                 315                 320

His Gly Ser Leu Pro Ser Ser Pro Val Gln Thr Pro Gly Ala Thr Cys
            325                 330                 335

Glu Trp Pro Val Glu Ser Pro Val Ser Pro Pro Val Pro Ser Leu Glu
            340                 345                 350

Gln Ser Pro Ala Thr Pro Leu Ala Ser Pro Ser His Ser Ala Ala
            355                 360                 365

Asp Leu Pro Pro Ala Ser Leu Pro Ala Val Pro Leu Pro Leu Ser Ser
    370                 375                 380

Thr Leu Glu Leu Ser Arg Val Ser Pro Gln Gln Val Gln Thr Thr
385                 390                 395                 400

Gly Ser Pro Pro Arg Ser Pro Pro Ser Gln Ser Ser Leu Ser His Arg
                405                 410                 415

Pro Pro Leu Gly Pro Ser Ser Val Gly Ala Ser Gln Thr Leu Pro Gln
            420                 425                 430

Arg Ser Ser Ser Ala Ser Pro Ala Gln Pro Val Glu Glu Leu Gly
            435                 440                 445

Pro Glu Gln Ser Gln Ala Pro Leu Ala Ser Ser Lys Pro Glu Gly Thr
    450                 455                 460

Thr Pro Leu Val Asn Val Lys Glu Ala Thr Ser Lys Pro His Ala Met
465                 470                 475                 480

Gly Asn Pro Thr Glu Asp Ser Ser Trp Met Ser Lys Val Phe Lys Lys
                485                 490                 495

Asn Lys Gln Lys Thr Ser Ser Thr Arg Lys Gly Phe Pro Arg His Pro
            500                 505                 510

Arg Ser Lys Lys Thr Gly Gly Lys Val Gln Ser Ala Pro Cys Pro Leu
            515                 520                 525

Asp Phe Thr Leu Leu Ser Thr Ser Glu Thr Val Trp Val Thr Tyr Arg
    530                 535                 540

Pro His Pro Ser Gln Ile Gln Glu His Ser Cys Pro Glu Glu Ala Val
545                 550                 555                 560

Asn Gln Glu Arg Thr
                565

<210> SEQ ID NO 3
<211> LENGTH: 1703
<212> TYPE: DNA
<213> ORGANISM: Canis familiaris
<220> FEATURE:
<221> NAME/KEY: CDS
<222> LOCATION: (1)..(1476)

<400> SEQUENCE: 3 atg gaa gag cag gtg ttc aag ggg gac cca gac act ccc cat tcc atc      48
Met Glu Glu Gln Val Phe Lys Gly Asp Pro Asp Thr Pro His Ser Ile
1               5                   10                  15 tcc ttc tcc ggc agt gga ttt ctc tcc ttc tac cag gcc ggg gct gtg      96
Ser Phe Ser Gly Ser Gly Phe Leu Ser Phe Tyr Gln Ala Gly Ala Val
                20                  25                  30 gat gcc ctt cga gac ttg gcc ccc cgg atg ctg gaa acg gcc cac cgc     144
Asp Ala Leu Arg Asp Leu Ala Pro Arg Met Leu Glu Thr Ala His Arg
            35                  40                  45 ttt gcc ggg aca tca gca ggt gca gtg gtg gcg gct ctg gtc atc tgt     192
Phe Ala Gly Thr Ser Ala Gly Ala Val Val Ala Ala Leu Val Ile Cys
    50                  55                  60
```

| | | |
|---|---|---|
| ggg att gaa atg gat gag tac ctg aga gtc ctc aat gta ggt gtg gct<br>Gly Ile Glu Met Asp Glu Tyr Leu Arg Val Leu Asn Val Gly Val Ala<br>65                             70                         75                     80 | | 240 |
| gag gtg aag aaa tcc ttc ctg ggg ccc ttg tcg cca tcg tgc aag atg<br>Glu Val Lys Lys Ser Phe Leu Gly Pro Leu Ser Pro Ser Cys Lys Met<br>                 85                         90                         95 | | 288 |
| gtg cag ctg atg cgg cag ttt ctg tat agg gtc ctg ccc gag gac tcc<br>Val Gln Leu Met Arg Gln Phe Leu Tyr Arg Val Leu Pro Glu Asp Ser<br>                100                     105                     110 | | 336 |
| tac aag gtc gcc aca ggg aag ctc cac gtg tcc ctc act cgg ctc acg<br>Tyr Lys Val Ala Thr Gly Lys Leu His Val Ser Leu Thr Arg Leu Thr<br>               115                     120                     125 | | 384 |
| gac gga gag agt gtc gtg gtt tca gag tat aca tcc aag gaa gag ctc<br>Asp Gly Glu Ser Val Val Val Ser Glu Tyr Thr Ser Lys Glu Glu Leu<br>130                           135                     140 | | 432 |
| atc gag gca ctg tac tgc agc tgc ttt gtc ccc gtg tac tgt gga ctc<br>Ile Glu Ala Leu Tyr Cys Ser Cys Phe Val Pro Val Tyr Cys Gly Leu<br>145                         150                     155                   160 | | 480 |
| atc ccc cca act tac cgt ggt gtg cgc tac att gac ggg ggc ttc acg<br>Ile Pro Pro Thr Tyr Arg Gly Val Arg Tyr Ile Asp Gly Gly Phe Thr<br>                       165                     170                     175 | | 528 |
| ggc atg cag ccc tgc tcc ttc tgg acc gac tcc att acc atc tcc acc<br>Gly Met Gln Pro Cys Ser Phe Trp Thr Asp Ser Ile Thr Ile Ser Thr<br>               180                     185                     190 | | 576 |
| ttc agc ggg cag caa gac atc tgt ccc cgg gac tgc ccc gcc atc ttc<br>Phe Ser Gly Gln Gln Asp Ile Cys Pro Arg Asp Cys Pro Ala Ile Phe<br>                 195                     200                     205 | | 624 |
| cac gac ttc cgc atg ttc aac tgc tcc ttc cag ttc tcc ctg gaa aac<br>His Asp Phe Arg Met Phe Asn Cys Ser Phe Gln Phe Ser Leu Glu Asn<br>210                           215                     220 | | 672 |
| atc gcc agg atg acc cat gcc ctg ttc ccg cca gac cta ttg atc ctg<br>Ile Ala Arg Met Thr His Ala Leu Phe Pro Pro Asp Leu Leu Ile Leu<br>225                           230                     235                   240 | | 720 |
| cac aac tac tac tac cga ggg tat gaa gat gct gtt tca tac ttg agg<br>His Asn Tyr Tyr Tyr Arg Gly Tyr Glu Asp Ala Val Ser Tyr Leu Arg<br>                       245                     250                     255 | | 768 |
| cgg ctg aat gct gct tac atc aat tct ccc tcc aag aga gta ata ttc<br>Arg Leu Asn Ala Ala Tyr Ile Asn Ser Pro Ser Lys Arg Val Ile Phe<br>               260                     265                     270 | | 816 |
| ccc cgt gta gaa gtg tac tgc aat ata gaa ctt gcc ctt ggc aac gag<br>Pro Arg Val Glu Val Tyr Cys Asn Ile Glu Leu Ala Leu Gly Asn Glu<br>               275                     280                     285 | | 864 |
| tgc cac gaa tgc agt cag tca agc ctc caa aca cag cag caa gaa tcc<br>Cys His Glu Cys Ser Gln Ser Ser Leu Gln Thr Gln Gln Gln Glu Ser<br>290                           295                     300 | | 912 |
| ata caa ctt cac aca cag agg gct cct gaa gga gaa gga aag ggc agc<br>Ile Gln Leu His Thr Gln Arg Ala Pro Glu Gly Glu Gly Lys Gly Ser<br>305                           310                     315                   320 | | 960 |
| cac ggt tca ctt ccg tcc tca cct gtg cag aca ccc gga gcc aca tgt<br>His Gly Ser Leu Pro Ser Ser Pro Val Gln Thr Pro Gly Ala Thr Cys<br>               325                     330                     335 | | 1008 |
| gag tgg cct gta gag tca cct gtt tca cca cct gtc cct tca ctt gag<br>Glu Trp Pro Val Glu Ser Pro Val Ser Pro Pro Val Pro Ser Leu Glu<br>               340                     345                     350 | | 1056 |
| cag tca cct gca act cca ctg gct tca tca cca tca cat tct gca gct<br>Gln Ser Pro Ala Thr Pro Leu Ala Ser Ser Pro Ser His Ser Ala Ala<br>                 355                     360                     365 | | 1104 |
| gac ctg ccc cct gct tcg ctc cca gct gta ccc tta cca ctc agc tca<br>Asp Leu Pro Pro Ala Ser Leu Pro Ala Val Pro Leu Pro Leu Ser Ser<br>370                           375                     380 | | 1152 |

-continued

| | | | | | | | | | | | | | | |
|---|---|---|---|---|---|---|---|---|---|---|---|---|---|---|
| aca | ctt | gag | ctg | tca | cgt | gta | tca | cca | cag | cag | cag | gta | caa | act act | 1200
| Thr | Leu | Glu | Leu | Ser | Arg | Val | Ser | Pro | Gln | Gln | Gln | Val | Gln | Thr Thr |
| 385 | | | | 390 | | | | | 395 | | | | | 400 |

```
aca ctt gag ctg tca cgt gta tca cca cag cag cag gta caa act act       1200
Thr Leu Glu Leu Ser Arg Val Ser Pro Gln Gln Gln Val Gln Thr Thr
385                 390                 395                 400 gga tcg cca cca aga tcc cca cct tcc cag tca tct ctg tca cac agg       1248
Gly Ser Pro Pro Arg Ser Pro Pro Ser Gln Ser Ser Leu Ser His Arg
            405                 410                 415 cca ccc ttg ggg cct tca tct gta ggg gca tct caa aca ctg ccc caa       1296
Pro Pro Leu Gly Pro Ser Ser Val Gly Ala Ser Gln Thr Leu Pro Gln
        420                 425                 430 cgt tct tct tca gca tca cct gca cag cca cct gtg gag gaa cta ggc       1344
Arg Ser Ser Ser Ala Ser Pro Ala Gln Pro Pro Val Glu Glu Leu Gly
    435                 440                 445 cca gaa cag tcc caa gct ccc ctt gcc tct tca aag cca gaa ggt acc       1392
Pro Glu Gln Ser Gln Ala Pro Leu Ala Ser Ser Lys Pro Glu Gly Thr
450                 455                 460 aca cct ttg gtt aat gtg aag gaa gcc acc agc aag cct cat gca atg       1440
Thr Pro Leu Val Asn Val Lys Glu Ala Thr Ser Lys Pro His Ala Met
465                 470                 475                 480 gga ata cta cta cta ctg aag act cca gtt gga tga gcaaggtgtt           1486
Gly Ile Leu Leu Leu Leu Lys Thr Pro Val Gly
            485                 490 caagaagaac aaacaaaaga caagtagcac cagaaaaggc ttcccaagac acccacgatc    1546
caaaaaaaca ggcggcaaag tgcagtctgc tccctgtccc ctcgacttca ctctgctctc    1606
cacttccgag acagtttggg tcacctacag gcctcatccc agccagatcc aggaacacag    1666
ctgtcctgag gaagctgtga accaagagag aacttga                              1703
```

<210> SEQ ID NO 4
<211> LENGTH: 491
<212> TYPE: PRT
<213> ORGANISM: Canis familiaris

<400> SEQUENCE: 4

```
Met Glu Glu Gln Val Phe Lys Gly Asp Pro Asp Thr Pro His Ser Ile
1               5                   10                  15

Ser Phe Ser Gly Ser Gly Phe Leu Ser Phe Tyr Gln Ala Gly Ala Val
            20                  25                  30

Asp Ala Leu Arg Asp Leu Ala Pro Arg Met Leu Glu Thr Ala His Arg
        35                  40                  45

Phe Ala Gly Thr Ser Ala Gly Ala Val Val Ala Ala Leu Val Ile Cys
    50                  55                  60

Gly Ile Glu Met Asp Glu Tyr Leu Arg Val Leu Asn Val Gly Val Ala
65                  70                  75                  80

Glu Val Lys Lys Ser Phe Leu Gly Pro Leu Ser Pro Ser Cys Lys Met
                85                  90                  95

Val Gln Leu Met Arg Gln Phe Leu Tyr Arg Val Leu Pro Glu Asp Ser
            100                 105                 110

Tyr Lys Val Ala Thr Gly Lys Leu His Val Ser Leu Thr Arg Leu Thr
        115                 120                 125

Asp Gly Glu Ser Val Val Val Ser Glu Tyr Thr Ser Lys Glu Glu Leu
    130                 135                 140

Ile Glu Ala Leu Tyr Cys Ser Cys Phe Val Pro Val Tyr Cys Gly Leu
145                 150                 155                 160

Ile Pro Pro Thr Tyr Arg Gly Val Arg Tyr Ile Asp Gly Gly Phe Thr
                165                 170                 175

Gly Met Gln Pro Cys Ser Phe Trp Thr Asp Ser Ile Thr Ile Ser Thr
```

```
                     180                 185                 190
    Phe Ser Gly Gln Gln Asp Ile Cys Pro Arg Asp Cys Pro Ala Ile Phe
                 195                 200                 205
    His Asp Phe Arg Met Phe Asn Cys Ser Phe Gln Phe Ser Leu Glu Asn
                 210                 215                 220
    Ile Ala Arg Met Thr His Ala Leu Phe Pro Pro Asp Leu Leu Ile Leu
    225                 230                 235                 240
    His Asn Tyr Tyr Tyr Arg Gly Tyr Glu Asp Ala Val Ser Tyr Leu Arg
                     245                 250                 255
    Arg Leu Asn Ala Ala Tyr Ile Asn Ser Pro Ser Lys Arg Val Ile Phe
                 260                 265                 270
    Pro Arg Val Glu Val Tyr Cys Asn Ile Glu Leu Ala Leu Gly Asn Glu
                 275                 280                 285
    Cys His Glu Cys Ser Gln Ser Ser Leu Gln Thr Gln Gln Gln Glu Ser
                 290                 295                 300
    Ile Gln Leu His Thr Gln Arg Ala Pro Glu Gly Glu Gly Lys Gly Ser
    305                 310                 315                 320
    His Gly Ser Leu Pro Ser Ser Pro Val Gln Thr Pro Gly Ala Thr Cys
                     325                 330                 335
    Glu Trp Pro Val Glu Ser Pro Val Ser Pro Val Pro Ser Leu Glu
                 340                 345                 350
    Gln Ser Pro Ala Thr Pro Leu Ala Ser Ser Pro Ser His Ser Ala Ala
                 355                 360                 365
    Asp Leu Pro Pro Ala Ser Leu Pro Ala Val Pro Leu Pro Leu Ser Ser
                 370                 375                 380
    Thr Leu Glu Leu Ser Arg Val Ser Pro Gln Gln Gln Val Gln Thr Thr
    385                 390                 395                 400
    Gly Ser Pro Pro Arg Ser Pro Ser Gln Ser Ser Leu Ser His Arg
                     405                 410                 415
    Pro Pro Leu Gly Pro Ser Ser Val Gly Ala Ser Gln Thr Leu Pro Gln
                 420                 425                 430
    Arg Ser Ser Ala Ser Pro Ala Gln Pro Pro Val Glu Glu Leu Gly
                 435                 440                 445
    Pro Glu Gln Ser Gln Ala Pro Leu Ala Ser Ser Lys Pro Glu Gly Thr
                 450                 455                 460
    Thr Pro Leu Val Asn Val Lys Glu Ala Thr Ser Lys Pro His Ala Met
    465                 470                 475                 480
    Gly Ile Leu Leu Leu Leu Lys Thr Pro Val Gly
                     485                 490

<210> SEQ ID NO 5
<211> LENGTH: 45269
<212> TYPE: DNA
<213> ORGANISM: Canis familiaris
<220> FEATURE:
<221> NAME/KEY: exon
<222> LOCATION: (501)..(705)
<223> OTHER INFORMATION: exon 1
<220> FEATURE:
<221> NAME/KEY: exon
<222> LOCATION: (23005)..(23237)
<223> OTHER INFORMATION: exon 2
<220> FEATURE:
<221> NAME/KEY: exon
<222> LOCATION: (24608)..(24673)
<223> OTHER INFORMATION: exon 3
<220> FEATURE:
<221> NAME/KEY: exon
<222> LOCATION: (25883)..(26092)
```

```
<223> OTHER INFORMATION: exon 4
<220> FEATURE:
<221> NAME/KEY: exon
<222> LOCATION: (27594)..(27654)
<223> OTHER INFORMATION: exon 5
<220> FEATURE:
<221> NAME/KEY: exon
<222> LOCATION: (35164)..(35748)
<223> OTHER INFORMATION: exon 6
<220> FEATURE:
<221> NAME/KEY: misc_feature
<222> LOCATION: (35164)..(35802)
<223> OTHER INFORMATION: alternative exon 6
<220> FEATURE:
<221> NAME/KEY: exon
<222> LOCATION: (38324)..(38402)
<223> OTHER INFORMATION: exon 7
<220> FEATURE:
<221> NAME/KEY: exon
<222> LOCATION: (40014)..(40139)
<223> OTHER INFORMATION: exon 8
<220> FEATURE:
<221> NAME/KEY: allele
<222> LOCATION: (40019)..(40021)
<223> OTHER INFORMATION: ACC replaced with TACTACTA in del3ins8 allele
<220> FEATURE:
<221> NAME/KEY: exon
<222> LOCATION: (43818)..(43923)
<223> OTHER INFORMATION: exon 9
<220> FEATURE:
<221> NAME/KEY: exon
<222> LOCATION: (44743)..(44769)
<223> OTHER INFORMATION: exon 10

<400> SEQUENCE: 5
atataactcc ttggctgcca cagcatgtca gagacagagg catcctctga taaccatcag      60
tgaagggttt tgcaactctg tgtgtgaagc ctcctgggct gagggctgag cagcgctgcc     120
tctttgggat ggccccagtg gcggctgcca acgctgctag gtttacgcag cctcctgggc     180
caagggctga ggagcctgtg ccagagatga atctagccac gcaatgacgc caggggggac     240
tcgcagaccc gagacgctgc tcatacattc agggtgcctt ctgcaccttg acctgggcct     300
gaggcctttg atcagcattt gggactgcct cctggaggag ctggatgggc ccaggcagtg     360
gctgctgagc cgtccgtggg tgtcccagcc gacccaggag agacggcccc tttccaggtg     420
ccgggctagc aggagagtgc ggccctgact tgcagcagga gcgcagccca ggaggcaagc     480
cttgcccagg ggccaaggag atg gaa gag cag gtg ttc aag ggg gac cca gac     533
                       Met Glu Glu Gln Val Phe Lys Gly Asp Pro Asp
                        1               5                  10 act ccc cat tcc atc tcc ttc tcc ggc agt gga ttt ctc tcc ttc tac       581
Thr Pro His Ser Ile Ser Phe Ser Gly Ser Gly Phe Leu Ser Phe Tyr
           15                  20                  25 cag gcc ggg gct gtg gat gcc ctt cga gac ttg gcc ccc cgg atg ctg       629
Gln Ala Gly Ala Val Asp Ala Leu Arg Asp Leu Ala Pro Arg Met Leu
       30                  35                  40 gaa acg gcc cac cgc ttt gcc ggg aca tca gca ggt gca gtg gtg gcg       677
Glu Thr Ala His Arg Phe Ala Gly Thr Ser Ala Gly Ala Val Val Ala
   45                  50                  55 gct ctg gtc atc tgt ggg att gaa atg g gtaaggcgtt tgttctggat           725
Ala Leu Val Ile Cys Gly Ile Glu Met
60                  65 tccctggggg agccttgggg gtgggggggac tccccaaagt ggggatgctt tgggaaacag    785
agccaggcct tctggctggt gggaagggaa ggttgagagg gatggcaaga agctgggaca     845
tttgaggttg gggtcagcca ggtcccagtc tctgagccac tgggtgagtg tggacccatc     905
cctccttctc ggtctcccctc aacatttctg tgacaccctg tctgccaggg cctggagggg    965
```

```
acaaaggcag tatctccctc aaacattctg gtcttggagt cacaccatga cacagtcaga      1025
cactgggatg gagtgtcatt ccggtttggc ctcttttgta gtgcacccat ccttgggtgg      1085
ggcagcactt tataccttta ttaccttggc agggtagctt ccaggtggct ggagaagtgg      1145
aagccttgtg gccacaggga acagccagac tgggaaagaa tcgggaaggt gtcccttcac      1205
cctctttcct gctgtcccgg gtcccactgc tgacccggag ccagaagcg ccatccggtg       1265 caggaccacc tggccgcccc acatggcagg cctagcccag cgtcctcaca gctgcctcgg      1325
atggcagtca atcctgcact gtgctactgc tcaaaggccg tgccccggga agcagaaatt      1385
ctagagaggg gagacagaaa aaaaacattc agacaggcaa ccttgtgatg tcacatcagg      1445
acaccataag atctatgaat aagattatag caggaaaggg gcagagaaaa gagaagctat      1505
tttttttctt tttttttttt taatcaaccc aaccttttat ctatttattt ataatgtatg      1565
tatgcatgta tttagtctat tacccagtta cccccttccct catcctcctc ctcccccagc     1625
aaccctcagt ttgtttccta tgattaagag tctcttatgg tttatctccc tctctgattt      1685
cgtcttgttt tattttttcc tctcttgctc tatgatcctc tgttttcttt tttctttttt      1745
ttttaagatt ttatttattc atgagagaga gaaagagaga gagagagagg catagacaca      1805
ggcagaggga gaagcaggct ccatgcaggg agcccaatgt gggactcgat cccaggactc      1865
caggatcacg cccttggcca aaggcgggca tttacctgct gagccaccca ggcgtcccta      1925
tcctctgttt tctttcttaa attccacaca tggtggacct cacatatggt gagatcatat      1985
gataattgtc tttctctgac tgacttattt cccttagcat aatatcctct cattccatcc      2045
atgtcattgc aaatggtgag ttccattttt ttgatggctg agtagtattc cattacatat      2105
atataccact tctgtatcca ttcatctgtc agtggacatc tgggctcttt cctcagtttt      2165
gctattgtgg acattgctgc tataaacgtt ggggtgcatc agatcaccac atttgtatct      2225
ttgaagtcaa tacccggttg tacgattgct ggattgcagg gaactctat tttcaacttt       2285 ttgaggaacc tccatactgt tttccagagt ggatgcacca ggttgcattc cagtggggc       2345 tattttagaa agagtggtca gggaagccct tttgaaggag acaacattca aacagagacc      2405
caagtgctgt gagagaacaa gccatttgaa gtgagggaaa gaattttcca gctggaggag      2465
catccaggga gccagggagt gggggcaaga agaaaggagt gggggcaaag ggtggagggg      2525
caggcggggg tcagatgaca cccacatgat gccttgtagc cagagcagca agctctgagt      2585 cacccctgata gctaaggagc gcaggcaggc tgtaagggg cgaagtgggg aggcagtgaa      2645
gagcacgtga tccaggtgga ttggacccca gctctgctgt ttcaccatgt ggacgtgagg      2705
cagactattg aatgctctgt gcctctgttt ctgcatctgt aaagtgggaa ttctactcgt      2765
acccaattcc aagagttgtt aaagggttaa ctgagctaga gtgaccagtt tatcacagtg      2825
cctggcacag ggcaactgcg tgggatgtgt caactccctg gttagggttt gtaaggaacc      2885
ccaacagctg ggcaaagtgc cttaggagga aagggcagc aacaaggagc ttagcgggag       2945
accacagcgt gtccaggcag gggtgagcac agcaggtgtc tgggtcttga ggggcagtaa      3005
gaagccagtg ggtttaggat gtactttgaa ggtggagcca gtgagacctg ccaaagggcc      3065
agctgcagtg tgcgaggaag cggtgccagc aggctgcctt cctgcctggg ggcctctgtg      3125
ctgggtgaga agtctttctt catcataaag aatattagtg atgcccattc actgagtacc      3185
tcttatgaac caggtaattt ttttacttct aatatttcac aagtaacaaa ttccttctca      3245
ctgtacaaaa ttcaaacaat gcaaaagtat atgtccttaa tcccactctt cctcctgtag      3305
```

```
ctagtctaag agatcatttt tttccaatta aaagcatttt aaaattccag tatagttaac    3365
aaagcgttgt attattttca gttcaataca gcgattccac aattctacac attgctcagt    3425
gcttatcatc ttaagtgtac tcttaatccc cttcacctgt tccacccatt ccccacccac    3485
ctcccctctg gttgctacca gtttgttctc catcgttaag agtccgtttt ggagtttgtc    3545
tcttttctc cttgttcatt tgttttgttt cctaaagtga aatcgcggta tttatctttt     3605
ccctgcctga cctacttcac ttaatatgct atcctcaagg tccatccatg tcgttgcaaa    3665
tggcaagatt tcgttttttt atggctgagt aattatctat tcatctctca atggactcct    3725
gggctgctat tataaataat cctgcaataa acatagaggt gcatatatcc tttcaaatta    3785
gtgtttttgt attctttggg taaataccca ggagtggaat tgctggatca tatggtaact    3845
cactttttaa ttttttgagg aacatccata ctttttttcca cagtggctgt accagtttgc   3905
attcccacca acaatgcacg agggttccct tttcccaca tactcaccga cacttgtttc     3965
ttgtgttttt gacttagcc attctggcag gtgtgaagtg atatctcctt gtggttttga     4025
tttgcatttc cctgatgatg agtgatgtgg agcatctttt catgtgtgtt ttggcccttc    4085
tacatcttct ttaatgcaca gagtcctctt tgaatgtagc agttcacttc agtcacacag    4145
tagaccctag aacaagcctt cagaaagggg ctgggtgaaa gcccacactc tcttgtctgg    4205
gagtcacaga attcctgtcc ttggagacat cctgtctctg ggattctctc cctttctggg    4265
tatgtgtgtc actcacatgc tccatcactc ccactctctt cgtgtcttta ttgcgacttc    4325
ttaaaagaca ctgtctgaga gagtctgtgg tgtttccacc ctctggcatt caaggatttg    4385
ccataattca ttcatttcaa tcagttccac cagtactacc aaaaacggac tcggccaggc    4445
tgcgagaggc atggacagca agtgagaggc actaaagcct aggaggacac ttaactgtag    4505
gtgcaaccaa ggccctgacc atgcacactg ccggtgatca ggacagtagt tcaaggagga    4565
gtgagatgca cgtgggactt gcccttgtca ttcagcagca tgtttatgag atttatccac    4625
gtcattccag ccaccttcat tcaggttaac tgccacataa ttcactgtta actagcactt    4685
ccttatacca ggcactgttc taagtctttg gtatattaac tcatccagtc ctcacagcaa    4745
gccccctgagg tgaaaactct tattgcctcc atttacagag gaggcaactg agtcacagaa   4805
ggcctaacta acttgcctac agtaataaaa agaagcatgc ggtaaagctg gggttagaac    4865
ccagtctggc ctcaccttt atttacatat ttatatttat ttttattaaa aaatttttt     4925
taagatttat ttattttaga aaaagagagt gtgcacaagt gggaggaggg acagagagag    4985
agaggcgggg ggcggggaag gagactctgt gctgagcaca gcacccaacg tggggctcaa    5045
tctcataatc ctgagatcat gacctgagcc aaaaccgaga actggacact taaccgactg    5105
agccacccag gcgcccctgg cctcaccttt taaactactc tgcttcttga cagagcaggg    5165
tcagggagtg cagatgctgg ttgtatggct cctggggtca ggaagtctct ctgaacagat    5225
ggaatttgca cagggacctg gaggggtga gggagtgagc cacgagaata tctgggagga     5285
tcattctaca aagagggaca agtgacttgt gtaacgtcct gttatcagcc agaagcagag    5345
caagaagcag gaccagattt cctgactttt attaaggatc tttacctctt tcagtatata    5405
ttccattagg actatatcat ggctcatcca gccattctgt tgatgcaaca gccttgtttt    5465
tgttataaac aactctgcca tgaacatcct tgtttgtatt tcatgcccac atgaatgttt    5525
ccctaggata tgcattcaca ttagcattac cagactaaag tattctctga agtggttgta    5585
ccaatttaac cactagcagc gtgtacaagt tctaatttc ccacaatgtc accagctctt     5645
ggtactgtca gacctcaaag ttctaagtca atctaatgaa tgtgatacta tatctcactt    5705
```

-continued

```
tactttgctt atttaatctt cctaccctga ttggtagtaa gcaatgttag gcatctccgt    5765
gtatttattg cctgtttgcg tgccctcttc tgtgacttac ctgtctgctt gtgaacttct    5825
cctgcctttt ttctctacca ttatcttgtt ctctttaact tgtagatgtt cttgatatag    5885
tctgtgcatg aattatgtca gttttaagca ttgcagctac actattccac ttcgtggctt    5945
gtcttcttat ttaaggatgt ctgttttca ctcagaaaat tttagtttta atatagtcaa    6005
atgtatgaat cttttccttt taacaacttc tgtgttttaa tatcttcact tgttacaat    6065 gagtcctata ttttgtttta aaagttctaa ggtgggacac ctgggtggct gagtggttga    6125
gcatctgcct ttggcccaca gcatgatcct ggggtcccgg gatggagtcc cacattgggc    6185
tccccacagg gagcctgctt ctccctctgc ctgtgtctct gcctctctct gtgtctctca    6245
tgaataattt ttttaaaaaa gttctaagat ttcttgctct tccattaatc tagctggaat    6305
ttattttgtg gctagtttga ggtcaaaatc aaaaattttc attgttttgc cacatgataa    6365
ccaatttccc cacaccattt ataggcaact gttttcacac tggtcagctc cctctagttt    6425
cattcaaggt cctggattct caagggtcca tccctggagt ctctcttctc tcccactggc    6485
aaatttgtag atttctgcac cacatctcgc tgttttaatc actgtagcct attgtgtatg    6545
gcaatccctc tctcctctgc cctttttcta atttcatctt caactattgc ctctgttatt    6605
catgctcttt cttccccct tatgaaagaa cttgggattt taattgaaat tatgtcttcc    6665
catttataaa tatagtctat ttcttctggc cttttatgtc atttaataag gattctgtgt    6725
cttttattgg atttattagt ttttgttgct atgaagaatg ggttcttttt tccaatggca    6785
ttttctaatc taatcgatta ttgttgatat aaaggagtgt tgattgtttt tgcacatcga    6845
tcttgttttg agcaaacctg tgaatgttct taatagttcc aaaagtttat tgatagatta    6905
tttcatattt tatgtgtaaa caatcaccgt atctccatat aatcagaggt tcatttcttt    6965
tctagaaaat ctttgaagtg cctgggtggc tcaggtggtt aagcctctga ttgttgattt    7025
tggctcagat catgatctta gggttgcaag atcaagcccc acgctgggct ctgtgctggg    7085
catgggccct gcttaagatt ctcttctgt ctccctctgc ccctccccac catcatgtgc    7145
acatgttctc tctttctccc tctctcttaa aaaaaaaaa agaattctcc aacacatggc    7205
atgcagggct tctctcctcc cggtcacagc cctcctcttg ttccagtatg ggctttctgc    7265
cctgggagag catgtttatt tccctcaaat gctaaggcag cagtgggtcc accttctgga    7325
aagtgtgcca agctctgtga taggaccaat ttggggtata tgaaaatgtt tgtaaaaaca    7385
cttagcacag tgcctggttt tcattagtaa tgcagtaaag gttctgttc attcattcat    7445 ttacttaaag atagatggtc ttagtgacaa ctggtggggg attcaggatt tccaagctgg    7505 acaaactgg gcctgggaac ttgtccccag ttgcataatt ttgaaaaata aaatttcttc    7565
ttattcaaga atggggattt ggtggactta aaaccccatc cccgctttag ctacttagca    7625
ccttttcccc cataaaaact atataagcaa gcccttcctt ccttcttcc ttccttcctt    7685 ccttccttcc ttccttccac aagtgttttc tgagcatatg cttggctctg cagaggacac    7745
agagaacaca aaatgaaact ctgtcttcgc cctcacggaa cttacagtct actcaaactc    7805
aaaggcagct gctgagtagg tacaacacaa gagagttcca actgaatgtt gaacaattca    7865
aaggcttagg agagcagagg aagggaacaa cacctccaat ggtaggaagc ctcgcggaag    7925
tggcatctga gctggcactt caaagatgag gagaagctcc acaggagggg ataggtaggg    7985
caggagccta gccttctaat gaggaccagg cattacagca caacagtaac acaacggggg    8045
```

```
aaacgtgatg cctccaggag gtggtgaact gagcaggttg gctgatgtcg gggccttgtg    8105
cgagagtcac agaagcagct ttgtctcagc aagagttgcc caagacggga aagaactggt    8165
cctgaagaaa ggagcatctg ccctcggaga ggcccacaca gaacctggaa gccacctgtc    8225
tggttgctgc tcccatgggt cccccttcatt tggtgcagtc actgagatga cccataaacc   8285
cgaggactcc agattccaag acctaaagga acagggaaaa atattattta tcttgtgact    8345
catcgtaaac ataattctaa aaacaagaaa agtttccatg ataggatact atccatacat    8405
gccataattt tatttttattt tatttttattt tattttaaag actttattta tttgagagag  8465
agagtgtgtg agagagcaca agccaggtgg ggaggggcaa agggagggg agaagcagac    8525
tcctcattga gcagggagcc ccaacacagg gctcgatccc aggaccctga gatcatgacc    8585
tgagctgaag gcagatgctt aaccgactga gccactcagg ctcgcctcaa atgccataat    8645
tttaatattc tcttcctgtc attaaaacga cttccattaa atcagtggtc ctctcagctg    8705
catattcgaa tcaccggggt gctttcaaaa tgtccactgc ccaggcttct caccaagtga    8765
attaatcaca ttccccccagg atagaaccca ggctctagtg tttattcaac ccccagcaga   8825
ttccactgtg cagccacggt ggtgacccag tacgcgttga aaacctacgt gtaccacttc    8885
cctaagactc tatgaatgtc tgaccaggca gtgggaatgg gttgggcatt tcatatgcaa    8945
acctgcaaaa cgcccatcac agtcctggac taatggcatt tctctgtctg attattaatg    9005
gggaatggct tttcccagga taaagagaaa ctgttgcctt aggttggatt agattctgtg    9065
aattcctctg gctgggccat aaatgaggaa gactgatttt gtgaaggggt tggtccatcc    9125
cttttctcttg gaccatcccc aggttgaaac cacttttcag agaagccagt ggacacccct   9185
ggcccagagc ctcccctggc tgtctttatt tttctccttt acaaccccct cctggccttt    9245
aacttgcaaa aaacagcttt attgagatat aattcacata ctgtacaatt cacccattta    9305
aatcatgcaa cagaatggct tttagtatat tcacaaagtg gtacatccat tatcgcaatc    9365
aattatagaa catttaatt acctccaaaa gaaagcctag ataccttagc tgtgtcacct    9425
ctcaattcct atattccccc caagcatctg acagtcgata atctactttc tgtctctgta   9485
gatttgttta atctggacat tcatatcaa tggcatcaca caatatatgg tcttttgtgt    9545
tcaatttctt ttatttatt atgcattcta aaatatttt tccttagatt ttatttattt     9605
atttgagaga gcgagtgaga acaagcccgg gggtgagtag gggggcagag ggtgagggag    9665
aagcagactc cttgctgagc agggagctct atcccaggat cccgggatca tgacctaagc    9725
taaaggcgga tgcttaactg acccaaccac cctaggtgtc cctcagttaa tttagcagaa    9785
tgttttcaaa tgcatcgtat tatagcctgt gctagtgttt cattcctttt tattgttgaa    9845
taatattcta ttgtgtggat atgacatttt atttatttat tcatcgggtg atttacattc    9905
gggttgtctt tgctttgggc tattatgaat aatgctgcta taaaccttca tgtacatttt    9965
taacacttat taataacttt tttaatgaaa aaatttcaaa catgttggag agggcaatac   10025
ctcgaccccc aaggacccat gttataactt tagtagttaa ttaccagcat ttaccaactg   10085
gatttcaacc acagactccc cgccccactt tgtttttgttt tgtttttat atttttttgtt   10145
ttgtaatgat tttaagctca gatggaagtt gcatggagcc tcgccaggct ctgttttctg   10205
tgccagtgtt ccagagcatg tatctctgtg cagataagga ctgtgagcct gaggaaaccc   10265
aagggaatgg gacaggttga tctgcttgca gcacagagag tgtgtgtgtg tggggtgggg   10325
ggtaggcacc tgcttggtag aggggactgt tctccagctc ttccccctg gtgaggga     10385
gggaccagga gacagagctg cctttcaact gagatcatca aatgactttg ttttgttctc   10445
```

```
taaaagtaat tatcttccaa tattgtcaca ctgccttctc aaaaatgcca accctggcct    10505
ctactctcac cacctccaaa cacccaaacc actaaataaa atattaaaag ggtggggccc    10565
aggatccggg ctgggtttgg gagcttttct tttcacttcc acagtaggca gtctcaggag    10625
atgtcagttc tctacctctt tggtcgagct gtttcctctc tgaggaatgc catctctgct    10685
tctctccctg tggatcagct ctccatcctc caagtgaatc ctgattccct tcaggcactg    10745
aatccctggt gttcccacag ccggctctag gataggcttg tctcaaaggc cggaatcgcc    10805
aggggaaagg gcacctgact aggaataagg ctctcgggac tctgagaact ggaatgtccc    10865
acagtcagat tatgagccta gcttgccaca tgcattattt tcacatggtc tttcacagta    10925
gagtttagta gggagggagg tgctacaggg cctgggcagg gcaccacggc accgttacat    10985
cctccacgta aaatgacctt ctggttttct ctcgagagat gttaccctcc caagacacct    11045
tcccatttta ccctactgga tctctttcca tgatctctag tttacccaca gaatctatcc    11105
acctgtccta gcacttgata tacaatctta tttcagatgc tgcatcttat ttcatcagct    11165
agattggttg agcaatctga gatcttatgg gtcccaaggc ttcacagact gcttgtcaaa    11225
caagaaatct tgataaactc ctcacgattg ctggccatgg gcaggcatga ccttgaatgg    11285
gttttcgcat ttctattttg gggttcacct gactcttaga taactttgta catttatgga    11345
tatgacttta cttataatac tagaatttca tagaaggaag gtcaaggagt ccaactttt     11405 cattttaaag gtaattgtat ttagactttg tgaaaggaag taactggctg aaggcagacc    11465
ttgcttaagc cagtgatttc caagctgtgt tctgaaaaaa aaccaaagtc ctatgggaat    11525
gagggaggtt gaggggtggg ggagggagcc agggaacagg gagagaacac acactgaagc    11585
tctgggacct tcctcagctt caaaaagtat agtcctgcta ttgtccattc tttttaaaat    11645
ttcatttaga ggaagttttc caagtgattt ttttttttaa gtttcaaaaa ccactgtttg    11705
agtataatcc acttaatgtg cagacaaaga aattgagggc cagattctgg ctgaattaca    11765
gtgagttccc gcagtgaaca aaacactgtc tgccctcata aagctgacat tgtcttggtg    11825
aaatcaagcc ataaataacc aaacacataa aaaaacatca gcatgcatgc tccaaggaga    11885
aaataaagca gaggaagggt gtggtgaatg attaaagggt gaagtttcag gtgtgcaggt    11945
caggggaggc ctctctcagg cagaaggaag ggaggaggag ccacatgagc tcagagagaa    12005
gaatgtgaga cctatggcac aggctgagag acctatggcc caaatgcagg ctgagagacc    12065
tatggcacaa atgcagttga actcagctgt ccttctggac agaaaatggt ctttaaaagg    12125
acctcgcaaa gcataggaga gggccggcag agcagtaggg gccctgcccc acatccatgg    12185
gcacagcagg acccagcaag accctcccat ggagaaggag tccaccacag ctgtttggtc    12245
tgcctcccac atgtgggcca gtgctgcctc aggcagctcc tcctacccca gaaccaaagg    12305
cctcctgggg cacttggagc caagggtggc tgaagttatt gtcactggca ggtggctcag    12365
gtgtattctc cgcactgggc ccagtgcggt ctcaggggca tgtgctggga ggacaagact    12425
actttgcaag aaccttgact ctggtaactc ctttctttt tttatttat ttaatatttt     12485 gtttatttat tcatgagaca cacagagaga ggcagagaca caggcagagg gagaagcagg    12545
ctccacgcag ggagcccgac gtgggactcg atccctggac ccgggatcac aacctgagcc    12605
aaaggcagac agacgctcaa ccgctgagcc acccggactg ccttttttt tttttaagat    12665 tttattttat tttatttat tttatttat ttatttatt ttatttatt ttattttatt       12725 taaagatttt atttttattca tgagagacac agagagagag agagagaggc agagacacag   12785
```

```
gcagagggag aagcatctcc ccaattcttc aagccaggaa ggagagcctc catttcccct    12845
gtgcgtgcgt gcgtgcgtgc gtgggtccgt gtccctgtgt gcctacgcgc cggcacgcat    12905
gcgcatatgt gtgtgcgcgt ccctgcgaaa ccctgggtgg gccctggctg ccgcgtgcgc    12965
ctccagaggc cgagtgtctt catcagccgt catccccagt tacctacctg cccggaacgg    13025
ccgcgtttcc tgtacagtca ctccgctctg agtcctgcct tgatgtcgtg ctattaacag    13085
ctatttatca agccctgaga gtgtgccgg cactgtgctc agcgcctcgc acgaatcact     13145
tgctctaatt ctctcgcaac cccacgaggc agacactgtg tttagaccca ttttggaaag    13205
gaggagacag gtgtttagag cggttggata acctgcccgg gtctatacag cagagccaag    13265
agtgagctct ctcttttgct tctaccttct ccgtcctcca atcacgagtt cacatgttgc    13325
tttgcgagca gcgggacagc tttcctgcca aactctgccc aagcaattat ttgcacgttg    13385
cctaagaaag tgagatcaca tgacataatc aatgcaaaaa atgactttt ataacatgct     13445
atagaagtga catcactgca tggtgatggt tgtaactcac tacggtgttg acatcagtac    13505
cttttaaatc actcaaagca atttgtgttt tgcatgttta acatttccag ccaagtggat    13565
aaaggttaat ttcccccaaa caatcctctc gactcttaag ttgaagagaa ttgaatggca    13625
aatctggtca aactctgtgc tggttacaca gtagaaacat ctaacgattt ggaaaacaac    13685
tcagtgatgt cctgcaaccc gtttcccca acgtccgcag gcgtgagctg agcccctgct     13745
gagtggcagg ctctgtgtgt ctgacagccc tgtcatccgt ggtggtttgt ttgtttgttt    13805
gtttttaatt tcaattatga taaacttta attctggaat attgctagaa ttacagaaag     13865
gttgctgaga tcatacagag agtttgatat gttcttcacc caattcccct ccctaatgtg    13925
agcatcttca taactatggt acacttgtca gcagtaagac atcaacgttg gtacattact    13985
gttaataata gatttcacca gttttctac tgatgtcctt ttttttctg tcctaggatc      14045
taatctggga tccctcactg catttcatgg atccatttct tttttttttt ttaaatcact    14105
ctgatttggt gactttttt ttaaagattt tatttattta ttcatagaga cacacaccga     14165
gagagaggca gagacacagg cagagggaga agcaggcacc atacagagag cctgatgtgg    14225
gactcgatcc cgggcctcca ggatcacgcc ctgggtgcag gcggcgctaa accgctgcgc    14285
cactggggct gccccatttc tattttttaa aaagattttt aatctattca ttcgtgagag    14345
acacagagag agaggagagg cagagacaca ggcagaggga gaagcaggct ccatgcaggg    14405
agcccgatgt gggacccgat cccggaagac caggatcaca ccctgggcca gaaggcaggt    14465
gctaaacagc tgagacaccc agggatcccc tatagatcca tttctaaacc aactcaactc    14525
agtattaaga tagcattgtc tttcttgctt cactttggga ttaacttcag caaagatagc    14585
aagctccatt tccaattcta tagggaaaac aggcaaacaa cggataaaca aacctccaga    14645
ccagcttgac tcccatttga gtcaagagtt gacccattgc tccaactctg accttgtgaa    14705
accaccacat taggaagaat ctcctcctct gctccagctc agggctttgt gcacattgat    14765
cgatgtgggg gcagcagcca agaccaggct tgacagagaa aactgctctg tggtttactt    14825
tctcacaacc cccagtctgg ctgagtcact gaagtttcta ccttccttat cagccgttgg    14885
aaagatcctt aacagcccag tagaaaagat attctctctc tctctccttt tttttttttt    14945
ttttcatttt tatttatttc ttagaggcgg gggagagcat gagtgggaga agggcagagg    15005
cagagggtga agctgactct ccactgagca gggagcctga tgcggcgctc ggtcccagga    15065
ccctgggatc atgatctgag ccgaaggcag atgcttaact gacggagcca cccaggcacc    15125
cctagaaaag acattctttg atctcctttt tcagctcatt ctttcactca ttttgttaaa    15185
```

```
catttattat taatttatta aattgggcat cacgggtggc tgggcggttt ggtgctgcct    15245
ttggccccgg gtgtgatcct ggagacccag gatcagatcc cacgtcgggc tccctgcatg    15305
gagcctgctt ctccctctgc ctctccctct ctctccaatc tgtgtttctc atgaataaat    15365
aaataaaatc tttaaaaaaa taaaaaaaat tattaaatta ataaacatat attaagttcc    15425
tacagtgtgc caggtactga attaagtgct ggggcgtaat ggggaacaaa acagaaatag    15485
tctctgcttg tgaaacatta aatagtttat ttattcttga atactgacca agtgatcaac    15545
tctgagctag gcaatgatgg gagagaaggg tattcttttt tttttaattt ttatttattt    15605
attcatgaga gagagacaga cagacagaga cacaggcaga gggagaagca ggttccatgc    15665
agggaaccct atgcaggact cgatcccagg accctgggat cacaccctga gccaaagaga    15725
cgctcaactg ctgagctacc caggcatccc aagagaaggg tattcttaat ataggccctg    15785
ccctgtcttc aaaggatgca gctagccaga gagacaggac aggccactca aaacagactg    15845
agctaaattg tgtggatggt aaggggagac agagagtgac tcctatggca tgaatggaga    15905
gagatggagg taacagaccg gaccatccga agtgtcggac agcgggggta gtgaatgtct    15965
ccaatcaaca gaaataaact tttgttatca tggtgtttga aagagggagg catgggtgtt    16025
cctctgcggt ggcaccctaa attgagcata tctggaatga agagatgttc agagatggct    16085
ttctgtctgt agagcagagg ctcacatgaa ggtctcttga ctaccaccc cctcatacac    16145 aaaacaaaac aaaaccagct tttaagacta aagggtgact agttcacagc tctcacatta    16205
tcccaggagc cccctcagta gtgcagggag aatctggagg gtaggacagg ccacagccta    16265
gaaaggagac aatgttggtt tctaccttgg ggcaggatcc caaagagact tctagatcca    16325
ccaaagaaaa cagagagaaa agagcagggg caatggccct cagaacattc tgaggttcca    16385
gaaaaccttc tggatacatt ccctgactgc ttgttttatc tcaaggtgat gggtagatcc    16445
ttcagtggaa agctggggag agtgtgccca ggttctgggg gagaggcaca caggcagagt    16505
gaggccccaa gtgcttggaa agagcccag gggcaccttg ataggaacct aggtgaggaa    16565
ccagtgggag gcactgctgt ttccatggca acctgaaatt taaaaaacag atatgaactt    16625
ttaaagccaa ttctctagca aactcttagg gttagaaaaa ggtctgtgtg aaagattgtt    16685
attatccgta ggacagtatt ggtttggggt tttgttttt ataagtgctt actaggtcag    16745
acttgttttg cctttggctg aagcctataa tgcattctga acagggtaga aaaatgtgag    16805
ttttgtcata cattctactt ccagcttttg ttaacatagg ctgtgaccca gggtatatcc    16865
acccttttca tttctctgtg catccagcca cccagccatc cggctgtatt tattgagctt    16925
aatcttcatt tgggctcaat ttcttacctg caaaataaga gaaatagtct ggtttcgcat    16985
tttgacctag gctcctagca ccttaggagt ttcaaggtgg tgctttcagc agtcaccttc    17045
ctagggtggg atgggcggc aggcagggtc tgacacccca cttggcttca actgttatgg    17105
ccctgttata agccgttata tgtattggat ttccacttga gatttctttg gaacaaaggc    17165
tccctgactg aaaaatcgct gccccagaag atctccatgg atcttccctg tggcaatact    17225
gtcgcttcaa gccaaactgt tttccagtca atgcccctgc agtgcagggt atggaaatag    17285
aatggtgaag gaaccagggt cactacccct cgggggctcg cgtcactgtg aggatagact    17345
gagattgtaa gcgtgaaaac ccgctcgggt gaaatgactg ttgttaagat aataatttt    17405 attactatag tgcagtcgcg cagtggaaat atacccatgg ggaaaggcag ccgataattc    17465
agcctgcagt tagggaccag gtaggagcag cagactccca ggggctccac acagggcctc    17525
```

```
ggagaattgc agggctttcc tgggaacgca gctctgctcg ccgccgcctc ccctggggct    17585
ccccgcgccc gctgctgcag ggggcggccc gggcgatgg gggggggtg ttcgctgtga      17645 ttggctgagc cggaggttgt tgctaggcta ccagtccgcg ggagactggg ccacgcggtc    17705
ccatcctcca ccgcagatct gtcccccact gccgacccca atcggccacc ccgtgaagga    17765
gattccccag cagtttaaag tggcagctgc caagtgccca tctttctagg attttttcac    17825
ttagcttgag gtctggtgga ggaggggaag agaagctgtt ttattctccg atcgccttga    17885
ataagctgct tgcctttctg gccctcagtg tcctccttcg attcctgagg tcccttcatt    17945
tattcattat gcatgcatgc attcatgttt attaagtgcc tcccatgctc ccggcaccag    18005
atcaggcgct agagacaaaa ggataaataa gatagagacc atccttgctc tcaggaagcc    18065
gggatgggga tggaggtggg tgaagcggtg gaagacatta gacatttaag caaataaata    18125
agataataaa ataaacattt atttaatccc tttccttcct cttcagtgat atttctaagc    18185
cctgtccctt ttccctgcta aatctgtagg gttccccaag ttgacaatgg agggagtgca    18245
gatgccaaca gtgcctttac tgcattacag ctgacctacc tatcaccttg ctgtgctctg    18305
aaacagaggg acactctcat ccccacagtg cttgctcttt tgcatcccaa aggaagcctg    18365
agcttacctc agcaaagata tgaggcagca atcatcatgg tcctctgttc agatgagaaa    18425
gctgaaagcc agaaacatca agaagacttc tacatggtca caagaattac tagcataacc    18485
taactgatag tgagcactta ttatgcacag agacttaaat aaaacaatct gcctcataac    18545
ataacaagtc agttaagtta ttattattcc tattttatag gtggcaaaat tgagactgga    18605
agaagttatt tgacttgcct gtgatagtat gtggtgaagc ctgagccttt ctgagaaatg    18665
gagctggtcc tagaaaagag taaaagactg tctgagtggc tgagacctgg cttccagatg    18725
ccctttaaaa tctcctagtc cccagatctt gtttatttat tttcctattg aaattcttgg    18785
cacaagagac tcataaaatt tgatgaattg gccacagtta ccaatacagt tgaccttgtt    18845
gtcgctccat ctatctggga tgatcctgcc ttcaagcttt tactgagtaa tgatgttgag    18905
tagctcttcc ctgtgagcat ctccatcgct tgcttctcct ccctaccagg ttttcatgtt    18965
tctttgttca catactgaac aaacattggg cacccaccaa acgtcaggag aggcttgata    19025
gtggatggat actcagaaag gtgagtatcc atccttgagg agttcccagc ttacagcaaa    19085
ggtttctgaa gggccttcca taggcaaagc gcagtgatag gccttagaga ggaaaggacc    19145
ataaggatct tcccccaaag aatcttcttc ttggcttggg agacagaccg aacttagata    19205
ataaaaggtg tgaaaagagg tgggaggaag cagaagtgaa tgtagcaagt gtgggttggg    19265
ggtgggagag ccaaccttga gtctcctgtg gtgctgcttt taaatcccat cttgccgtgg    19325
tcagtgtggg aaagtgtgtc ttagagccca gcagcatgca gcttggaagg aggccttta     19385 atgggagaag gtgctggaaa gtacagagat gcataaagaa gcaagctaaa tttatccctt    19445
ctcccagcac ccagcaatcg ctatgcttaa cacttgactt tctaccaaca gagacttgtt    19505
taaccagaag attagtcgct tctccctcgg ctggaaaag agagaaaaaa gagagagaca     19565
catttaagca tcggccttcg gcttgggtca taatatccgg gtcctaagtt tgagccctgc    19625
gttgggctct ctgcttgaca gggagtctgc ttctccctct ccctctgtac tgtctctctc    19685
tcaaataaat aaataaataa ataaataaat aaataaataa atctaagaaa gaaagggaaa    19745
aaaaggagag acagtcaaaa agagacagaa gaagggatgg tcagagactc taaagacaga    19805
gacacagaga gacctgaaaa gaagtaggag aggcagggat agaggcggcc tctgctacag    19865
agtaccaggg agcagcagga aagaatttga cactgggcgc ctgagtggaa gaaatcagac    19925
```

```
aatctcctgc cccctccctc cctgactaca tgatcctggc tagagcactg ctaatttcta   19985
gaaagcacaa ttttcagatg tgagtatcct ggagatgtct gtactattcc tattgtcttg   20045
gtcactgatt tgtctctgtc acccatcacc actcctgaat agctgagaat ggactgtaaa   20105
tgggtgatac acaaaagcca cgattaaaat aagcaataca agatgaaata tgcatgcctt   20165
tgacctagca tttccacctc taggaattta tcctaaggac aataattaag gacataggtt   20225
aaataaaggg ggggggggca tgagattatt ccctgcagca ttgttcagaa aagcaaagag   20285
caaactacat agctaacccc taccaggcac ctgctcagca aataatggtg taacctgaca   20345
atagctttcc atgccgcttg taaattgggt tataaataga cacttattga tgtggaaaga   20405
tgttatttat taggttaaaa aacccaacca agttacaaaa taatgtatat agtatgactc   20465
catgtaagta ttattattag taagaataca tataaaacct atagtctagg aagacataaa   20525
ctagatgtaa tctctggttg gagagatgcc cagacacttt attttttttt tcttttggca   20585
tttctgtatt ttaaaaaatt attttttgcca caaggaacat gtgtttcttg tgcaatggga   20645
acaaatttcc ttccatcaat cccagtgagc atctcctgcg gggagtccag gtgtgtaggg   20705
gcaagctgaa ccagttgttc ctggctcaga ggcattgtgg gaaaggccaa ccaacccatg   20765
caaggccatt tgagctgctc attaagaatt ccacaaacag catgtcccca gcctggtttg   20825
actcccgtcc tgactggtct ggtgggcaag aactcagtga cgtagccact cggtatccac   20885
atgcagttgc ttcgtaacta ccggtgagtt ggccatagct ctcccttgag ggaaaacgct   20945
gttggtacaa gttggcacat ggtaaagcta atcttgctaa aaccctaggt ccttcccacc   21005
tcccggggac accttcccct gtaacaggat gacggccagc atgttctgtt gctctggtca   21065
gtctctacta cacagatgca gtttgattct gaacgttggg aggcgggagg ccgtcactat   21125
ggcaacccag gcttgctcgg cctctgggat cagtccaaca cccgggaaag aaggtggggt   21185
ctagagtcag aacaaacatt gcggggctat ctgacctcac gcgaggcact tagcttttct   21245
ctgcctcagt ttctacaccc ataaaatgat gctgaagctc tttatcctac ccacctccag   21305
gataaactgt aaaacatgga aggagtagcg cagtcctagc tttcatttgt cttcaaattg   21365
ctgtgtgtga gtttgagaga atcacttaac ctctccatgg ctcagccact ctatttgtaa   21425
ataggaatat aacatccact gtgatgactt cccagatata ttgtcaggca tctgtaagaa   21485
tccagaatcc acatgttgga aggaatctta gcactcacgc aggaatccct ttgataaacc   21545
ctctggctga ggtgcctgtc cctcctttgc ttgattacct ccagtggcag agagctcatg   21605
actgcccaac ttcccaaata accattgcta ccatgacact aattgtaaga agttcttct   21665
gtataggatt tcttacagtt aaatatttat tttaaaacat tggcaatcct tttccgagct   21725
attgctgctt ctgattttgc cagagggctt gcacagggta gaaattagca gcaactggca   21785
aggagcaggt ccaggcccag ctctagaagc ctgtggttta gtgtaaaggg aaggagtgtg   21845
ggttctggtg tcacacaccc caggttaaaa tcccactttg ttcaattgcc aggcagctgg   21905
tcttgggcca gttatagtat ctctctgagc tgcagtctcc tgatcagtga aatgaggcta   21965
gaaatgccta cctcatagtg ttgccaggag aatctggcat gataacagtt ctcatcgaaa   22025
ttacacccctt aacttccgca ggaaattcta gggattggga ggacaggtaa caccttctct   22085
gtgatcccct gaacaacaca tctgcccgcc aagccccatc tggcacatgt agactcttat   22145
gtgacctgac tgtgctcctc tcagaaagag ggagaaagtt cctctccagg cccttgggac   22205
acctgcagcc tggcctggcg cagtttgtgc tccatatttt acggccttct ctctctcagg   22265
```

```
                                                        -continued
cctgtaccag gggtcctaaa gggaagatgc atgcaatggt tcaagacac aattcacttt   22325 ccctataatt cacctgcctc agggccagca ccccctccct gcccacagat attgtgggca   22385
ctaagctaag tgtcacaggg tgtcacttga tgaaggcttt caactgtatc agtgtgttta   22445
tttaattttt ttcaaagatt ttatttattt gacagagcaa gagagagagc acaagcaggg   22505
gagtggcagg cagatggaga gggtgaggca ggctcccact gagcaaggag cccgatgcag   22565
gactcgatcc cagaaccctg ggatcatgac ctgagctgaa gacagacgct cagctgactg   22625
agccacccag gtgcccctgt atcagtgttt taataggaat ctcatatagg gcaaaaagtc   22685
tctaagactc caaaagaatg tagtctggtg gtagatttcc atgcaagttg ggtaggcat    22745 ggggtccttt gccctcaata tgaaagggt caggatgcct gcatcaagtt tggccatcga    22805
ctagctgcag gctccctgga gccagtgact taattcttct gtgccttgct ttcctcatgt    22865
gtaaaacgac aggttgattc cagagaccaa cactgcctca gaattctagg gtttcccgtg    22925
ttggctgcag cctgattgcc actgacctct cttgtccaca agcagctgac ctgccccctc    22985
ctttctgctt cctccacag at  gag tac ctg aga gtc ctc aat gta ggt gtg    23036
                     Asp Glu Tyr Leu Arg Val Leu Asn Val Gly Val
                         70                      75 gct gag gtg aag aaa tcc ttc ctg ggg ccc ttg tcg cca tcg tgc aag     23084
Ala Glu Val Lys Lys Ser Phe Leu Gly Pro Leu Ser Pro Ser Cys Lys
80              85                  90                  95 atg gtg cag ctg atg cgg cag ttt ctg tat agg gtc ctg ccc gag gac     23132
Met Val Gln Leu Met Arg Gln Phe Leu Tyr Arg Val Leu Pro Glu Asp
                100                 105                 110 tcc tac aag gtc gcc aca ggg aag ctc cac gtg tcc ctc act cgg ctc     23180
Ser Tyr Lys Val Ala Thr Gly Lys Leu His Val Ser Leu Thr Arg Leu
                115                 120                 125 acg gac gga gag agt gtc gtg gtt tca gag tat aca tcc aag gaa gag     23228
Thr Asp Gly Glu Ser Val Val Val Ser Glu Tyr Thr Ser Lys Glu Glu
        130                 135                 140 ctc atc gag gcaaggggca gggcctggac caaggggtgg ggcccagttt              23277
Leu Ile Glu
    145 ggggaaacag tccccattc ttggaaggag tgaaatatca ccaaatgggt tatcacttag    23337 gaaagggcac tctgggagct tattctatac tcattaatat aaatcttagt tatgaattat    23397 tattgttgga aagtgctgtg gatatgccca gttttctttt gggacaaaaa ggtcaagtgg    23457 catgaccctc tgtcccttat ctcccctccc ctctcctctc tggaatacaa ggcccttgcc    23517 atgcagactc acagcccat gctggcatgg ccatgatctt gggggtgaag aatgaatggc     23577 agtaggcatg gacacctcct tcacctacct cacgtcctcc tggatttatt agcactcagc    23637 tcttcaagac ttctctctcc tggccaccta ccagctccca ctcttgctcc tgccaacgag    23697 agtgaaccat atacaaagca gacctctgta cctttgcacc tgctgtgcca tctgcctagg    23757 atgcctttcc cccctcccag cttgcttcac ctgcttaaca agacactagt cactctgcct    23817 tggaacttac cttcatcatc tgtctgcccc gcactcccct gggctgggca ctcctcctta    23877 ggggccgcaa tgcccatgct cacttccttc acagcccctg tcacccttgt actgtcacct    23937 acttgcttac tctccctcat tgagcattct caagggtgag catcttaccc tcctttgatt    23997 ccagagcctg gccaggaca cacacacatt aatggttgct gaattccatt gaattcatgg     24057 agatatgggg ctagaaggaa ccctggaggt cactgaggct gccctgtctc tttaaaaccg    24117 gaatcttggg gatccctggg tggctcagca gtttggtgcc tgcctttggc ccagggtgcg    24177 atcctggagt cccgggatcg agccccacga caggctcccg gcatggagcc tgcttctcct    24237
```

```
tctgcctgtg tctctgcctc tctcaatctc tcatgaataa ataaataaat acatcttaaa   24297
aagaaagaaa gaagaaagaa agaaagaaag aagaaagaaa agaaagaaag aaagaaagaa   24357
agaaagaaag aaagaaagaa agaaagaaaa agatacctt  aaaaaaaaaa gggggggggg   24417
atcttgggac cagactacca acacgttcac agggacgcag ctctttgggg ccaggccagg   24477
aattgaacct ggggctctgg tccccataac agtgcctctg tcttggattt aagaagggcc   24537
aggctgctga ggaggcctcc ccatccagcc gccagagcct caggcatctc tgctggttct   24597
ctccccacag gca ctg tac tgc agc tgc ttt gtc ccc gtg tac tgt gga      24646
            Ala Leu Tyr Cys Ser Cys Phe Val Pro Val Tyr Cys Gly
                150                 155 ctc atc ccc cca act tac cgt ggt gtg gtgagtgctt cggcgtggga            24693
Leu Ile Pro Pro Thr Tyr Arg Gly Val
160             165 gaggatgagc caggacccag gagtgctctg ggcccataa ctgggagatt agagggggtgg   24753 tctcagaatt cagtgggaag accaagagtt ggaaagattc ttgtgttttt ctacttctaa   24813
ttcccagtgt ggatggattt ctggggcttt gaggtgaact ttccctccat acattgggct   24873
tcactctgga cccaccaacc cattactgag cctggctagt caagactcca taggcttgct   24933 ggatttctc acacttgaca gagggtgtag aataagaccc tgtgacattg gtaccggaac    24993
tgtgattgac aaggaccttt aaagtcatct aggctagagt acatgaatca cctgggtca    25053 gagggagtca tgtaaactaa tgcaaattct aattccctag gcctgggcca gggccagaga   25113
ctctgcccct cagaccagcc acggctaacg ccagtgctgc tggtccacgg accatgcttt   25173
gagtaggagg atctaaccca tgtctcttct tcattttata tggaaagaaa atgagatcca   25233
gaaatcagga ttcagctaag agatggagca catattgcac atgtcagccg tgtacttctc   25293
aggcacccca gagaagtatt tgtggtcctt tgttcaagat tgaggcaaca gaagcccat    25353 gagggaaggg atatgtggcg gccagtggcc aggccagggt cattctgag agtgccaggg    25413 ataccgacc tcaacagagg gaggcagtgt agacacacag cagtctggag aggggatatt    25473
tcccagcctg ctcagaccca ctatgtgttc acattttcaa aaggcatgg gaacaggctc    25533 cattccctgg ccctgccctt agcagttgac tggctcagga gggtagcct gggagaggga    25593 gctgtgactg gggagcattt gttcatgctt tatccagatt ataaatgtcc ctctccctgc   25653
agaggcctgg aagccccagt ctcaggacca tagagatggc tgaggacaga cagtgaggga   25713
cagagcactg ggctgggggt tcaaggatca cgtggacaca ccacttaccc acctggacct   25773
tggtctcaag gcttgtccca agggactcat ttcctggggg tactccttga tgggggaaaa   25833
ggaactctga tcccatgagc atttattact ctgcctgccc cccccatag cgc tac att   25891
                                                        Arg Tyr Ile
                                                            170 gac ggg ggc ttc acg ggc atg cag ccc tgc tcc ttc tgg acc gac tcc    25939
Asp Gly Gly Phe Thr Gly Met Gln Pro Cys Ser Phe Trp Thr Asp Ser
            175                 180                 185 att acc atc tcc acc ttc agc ggg cag caa gac atc tgt ccc cgg gac    25987
Ile Thr Ile Ser Thr Phe Ser Gly Gln Gln Asp Ile Cys Pro Arg Asp
            190                 195                 200 tgc ccc gcc atc ttc cac gac ttc cgc atg ttc aac tgc tcc ttc cag    26035
Cys Pro Ala Ile Phe His Asp Phe Arg Met Phe Asn Cys Ser Phe Gln
            205                 210                 215 ttc tcc ctg gaa aac atc gcc agg atg acc cat gcc ctg ttc ccg cca    26083
Phe Ser Leu Glu Asn Ile Ala Arg Met Thr His Ala Leu Phe Pro Pro
220                 225                 230                 235
```

| | |
|---|---|
| gac cta ttg gtgagaggag gggcccagaa gggagggaga aggtgacagg<br>Asp Leu Leu | 26132 |
| gcctgggggt agggttgggg agccaatggg gtccatgcat ttccatttgt gtctccttaa | 26192 |
| acttcctcct aaacctgtat cctcgctttg ctgctaccta gctatgtgac cttgaatgag | 26252 |
| gccccctatgt gctctcagcc tcaatttct cccttgtaaa atgagatgat atcagaactg | 26312 |
| ctgataggaa tcttacctga acttttccac tctgacatac aatgtaggca acagcagcca | 26372 |
| tggcccatga gccaaatcca gccagtggct tgtgttttgt tttcaattt caatttccaa | 26432 |
| aactgctctt aaaaaaataa agtctacatg tctttccaaa tgtatgtctt tctccaacac | 26492 |
| agaagggtga acctgggaac aggcaccacg tttaactcac ttttttact acactccacca | 26552 |
| tgtctgcaga aggcattgct tatagaaggt tctcagtaat tgttgtttga atgattaact | 26612 |
| cctctgagcc agttttgtga cttgcactct aattattgtt tacaaaactc ataatcaaaa | 26672 |
| cactattaca cttagtcagg ctatggatac acaaggtatt ttattcatct gattgacttt | 26732 |
| gtcctccaac agttgcgtta ggaattccag catctgcctt aaactaattc tttggtaaag | 26792 |
| attatgtcta tttactttct taaaagcaat ccacaaatag gcagttcaag aaagatagaa | 26852 |
| cacaaatagg cagttcaaga aagatagaac aaatgcattg tattcgtcag agcctctaga | 26912 |
| acttgagttt ctgctcacaa tcagtgcctg acttccattc tcaaggtggc ttattttat | 26972 |
| atagcctgtg agctgagaat gggctttcca ttttcagagg gttgtagaag tagaagaaag | 27032 |
| agaaggagaa ggggaagaaa gaaaaagagg agaagaaaga ggaggaagaa gaggacaaga | 27092 |
| acaagaagag ataatctgtg gctttcaaag cccaagttat tgaccatctg gcccttatg | 27152 |
| gaaatgcttt gtgagcaatg ataacccatg taatcctcca gaatcctttg caatagatac | 27212 |
| tatcatattc ccatttaca ggtgaagaaa tcgaggttgt gagaggctac agccacacag | 27272 |
| caccaggatt tgaacccagt ctccaaattc tgctcttctt atggcccaaa tgcaccttct | 27332 |
| ctggctctgc tataaatatc tctcctgccc aggggaagct gatgatcagc tagaaatggt | 27392 |
| ttaacacatt aatgcactgt cactatggac ccataatctg caactgctcc ccacttctca | 27452 |
| gcagatagtg aggaatggaa cactggatgg gtacattctg aaaaatccat caaataaagc | 27512 |
| tcaagggcca tgaggtgagg ggacctcggc tctctccatt gctgcagcct tagtcacttt | 27572 |
| cctgctgtcc cctccttgca g atc ctg cac aac tac tac tac cga ggg tat<br>                                  Ile Leu His Asn Tyr Tyr Tyr Arg Gly Tyr<br>                                    240                245 | 27623 |
| gaa gat gct gtt tca tac ttg agg cgg ctg a gtaagtacgg ggtagggccc<br>Glu Asp Ala Val Ser Tyr Leu Arg Arg Leu<br> 250               255 | 27674 |
| ccaaaggggt gggttggggg gtggggtaag acaggaagta aagggctga gtccaggagc | 27734 |
| attgtcctaa aaagagaacc cgagatgccc ttccccagga gggctgggaa tgggtgcaag | 27794 |
| gacctggcag cttgcgttgt ccaggacaca ccactgtggc caaacattag gatctccatg | 27854 |
| gaaaagtggt cttagggtc actgctggga cagtcgatat gttttcatac aaatatattt | 27914 |
| ctggatttaa ggactgtgtt taggaaacac catagcttgt atcttcccgg aacattccat | 27974 |
| tttcaggtca tttcacttca ttctctttcc aagacaattg cattgttaat gcagaactag | 28034 |
| acatgatgag tttatatttg ggtaagactc caagagacat tgatcaacaa aggagagggt | 28094 |
| ctgtgtccaa caaatgttgg tttagcaaat atggtcccct acacctgcaa atggctccgt | 28154 |
| gcatccttgc ctgaagatt ccaaaggcat gtatttaca cgctaactcc acgaagacca | 28214 |
| tggcaaacgt ccctgacaaa aggaaagaaa aaatcttt gcatatttag aattgtttcc | 28274 |

```
atagaacata tttccagggg gaagaaagga ttccgggatt ggatggtgtt tacctaatgc   28334
tgttgaagtg ggggtttttg tttcccaggt tgtcatgtgg tctttgtgac tgtcttttt    28394 ggcaatcctg tgatattcca tgacagttga acagaaactt tgatcattcc tttgaatttc   28454
caaatgttca ctattataag caatactgtg gtgaacttt tgtgtacata gtttaaaaaa    28514
atattttagg agtgagttaa gggattgaat gtgggttttt ccctaggatg tgttggctat   28574
ttttccttca aagctgcttc ctgctttccc aagctccctt tgtcttgact cttccctttc   28634
tcctagggcc attctccgaa caaggggtgg ggagaaaagg atggagggac tgtgagttct   28694
ggaggcaagt aggtctgggc caggattctc atccccctg gctgtgtgaa ctcaaggaaa    28754
tcacttgccc cctctgtctt gattcctaac ctgtaaaaag gattaaattg ttgttcctga   28814
cacctactaa ctgtgtgatc ttgaacaggt aattcatctt ctgggacctc agttttctca   28874
tctgtataag ggggctgacc atggaactta cctcagaatt atattcctag acacagtcat   28934
tccagcccac tgaccctgtg ataggagt cagggccatc ctctcacctc cctggggag     28994 agactcctcc tcaccccgac tctgcttgga caactctcct cttctccaca tttacatgag   29054
tgacatctct gaaaactatg ccaagcgtcc aaaagctgga ccacctgagg ggtgttagtg   29114
gagggttaag atggagtctc acctatggag cctccggaat aggaggggct ggtgagggcc   29174
tggggtcctt tccaccacca gctgggaaac cccttcactc tttcctcagt gatggtgtgt   29234 actgggatg tggtgttggg ggatcccctg atttgggacc aattccctat gtcaggagac   29294
ccctctacct ctcaggttcc agcctggctg cctggctacc accatacctg tctttcccct   29354
aaaacttctt tctcttcctc tcagggcaag cctaaggaga gttacaaagt gctttgcttt   29414
agcatctctg gtgtccctca ctcctcaata gcctctggaa ggaacccagt gccatctcat   29474
gcccccacac tcttctaccc ttaggtgata tgaacaccat ggtctaaatg gcagtcttaa   29534
accgaaggat gctctaatag gagcattttg ggtatccatg aaagaatcag ggcagagtat   29594
ggaggctggg gggctttccc aggggccatg gaatcactcc aagtaggaac tgacacactg   29654
tgtaaggaaa aaatgtctct tgctggctac tgactatttt ttattcctct tccaatttgc   29714
cagtgtttgc atggctttct cagtgcaggt ttcttcagct ccaccctaga tcctcttagg   29774
tttggtaggg ctggattttc ctcccagcac cagatgcgag caggaggtat gacgcatctt   29834
gagaaattgt ggccagtgcc cagagccaca ctcttaattc ccacctccca tctgggaaca   29894 gaaaaaacg agagtccgcc ccagcctccc acccacccta ctgctttctg gatgggggtc    29954
agctccagca gaaggctaca cctgcaaagt gtcaccctca attcctccac tcacatcctg   30014
gcatctccct ctgctgccct ccttagggct caaatccacc taattattcc tgctgccagg   30074
cgagcttccc tctccaccct tggcctcccc tggcagcagc cttctgccaa agggaagggc   30134
actgcttgct ggcatgcttg aaaatccaca ttccccacac agacatgtgg acgtgggtgc   30194
tgagtgaggt tggagctcag aggatgccat gtctaaaata atccagctgg catccaggcg   30254
tgcctggcca gaccaaccca tccatccttc tttcctcctt ccctctccct ccctcccttc   30314
ttggcattct tccttctctc acaatttgtt aagttctctc tctctctctc tctctcacac   30374
acacacacac acacacacac ctacctatga aactaatacc acaatcaaga gagtgaacca   30434
ttatccatca tgccccaagt tttccttacg ttcttttgtg accctcccca ccttccccca   30494
gagtccccaa tctactttct atcattagag aaatttccta ctggacttac agtatgggct   30554
ctattttgtc tgcattcttt cactcagtat aattattctg agattcatca tgttattgca   30614
tgtataaata gttcattcct ttttaatttc caatccattt atgaaaatcc cacagttcat   30674
```

```
ttctccattc accaattaat ggacatttag gctgtatcca gtttgggcta ttatgaataa   30734
aactgctgtg aatactcatg gagtctttct atgaacatat gctttcattt ccttagggta   30794
aatacctagg agtggaatgt ctacatggta tggtaaatgt acatttaatc tataaccgta   30854
tttacgtaac atacaatatt atatgtgtat aattaaggta aatgcataac acaaaatcta   30914
tcatcttaac tattttttag attttttta tttttaaaa atatctctac actcaatgta   30974
agttgaactc acaaccccga gatcaaaagt tgcacgcttt tcccactgag ccagccaggt   31034
gccccactat cttaaccatt ttaagtgtac ggtttggtag tattatgtat agtcacattg   31094
tacaaccaat gtccagaact ttttcttact gcaaaactga aactctatac ccattgatca   31154
gcaactcctc atttctccct ctcctaggcc atggctacca ccattctatt ttctacttct   31214
aggagattga ctactttaga tacctcatat caatggaatc atacagtact tgtcttttg   31274
tgactggtgt atttcgctat cataatttcc tccaggttta tccatttgt agcatgtaac   31334
ataccacatt ttctttatca atgaacaatt tgaattgctt cttcctcttg gctattgtga   31394
ataatgatgc aatgaacatg ggtatgcaaa tatccttgtt tcaattcttt gggatataga   31454
gtaaggacat atatccagaa tgtatgttta acttttaag aaactgtcaa attatttatc   31514
gaagtagtcg tatcatttta cattctcacc accagtgcag aagagtacca gtttctctgt   31574
attatcacca acacttgaaa tggtcagtct tgttaatctt agctatgtga atagttgtgt   31634
ggtggtatct tactgtgatt ttaatttgta tttccttaat gactaatgat gccgagcatc   31694
ttttcaggtg ctaatttgcc atctatatta tatatcttct ttattgaagt gtttaactct   31754
tttggtcatt tcccacctag acttacaata agctttattt ttaaaaatac ttttagattt   31814
ccaggaaaaa atatgaaaat agcatggaga gcttccatat actttacatt ccctattatt   31874
atgtcttaca tttgttatat gttatagtat ggtatatata aaatttggta catagtatag   31934
catcgtgttt acaattaata tgctaataat ggttattatt aactgaagtc tgtatgttca   31994
gatttcctta cttttcaacc taatgtcctt tttctgatcc aggatcccat tcaggatacc   32054
acatcacatt ttaccatgat gtctctttag gttcctctta tctgtgacag tttcccagac   32114
tccttgtttt taatgaactt ggtagaatgg agtactggaa tattccttag ttggggtttg   32174
aggttgcctg atgttttct caggattagg ctggagttct cagttctggg aagggagatc   32234
acaaaggcaa agtaccattc tcatcacatt atatccaggt gcatgctatc tacatggctt   32294
attattcatg atgttgggct tggccatttg tctgcagtgg tatttattgg gtttctccct   32354
gtgaagttgc tctttctccc cctttctctt tgaaaagaag taactatgca ccacctgctt   32414
aagggatggg gagttaagct tcacttcctt aaggacaggg taatctacaa aaattatttg   32474
gaattcttct ggttgggaga tttgtctctt ctccctatt tgtatacttc ttcaattcct   32534
tgtttgtttc agtatggact cctggatact cattttatac tttgggctat tattcaggtt   32594
tcctttattt attttgctac tcaaattggt tcagctttgg ccattggaag ctctttcagt   32654
gggctctttt gcccatctta aaaattgaat tgtttgtttt cttatttaag aacttttatg   32714
tagttcagat aaatgctctt tatcagaaat atgatttgta aatatttct ctcagtctgt   32774
aatttctctt ttcaagttgt taagtcttct gaaaggtat ttttaatttt gatagggccc   32834
atattattaa tttgcttctt ttatggatta tgcttttggt gtttaatttg cttctttat   32894
ggattatgtt tttggcgtct tatctaagaa atctttgcct tcctcaagat cacaaaaagg   32954
ttttctccta tgtttctttc tagaagcttt atagtttttt ggtttttcat ttgtgtctat   33014
```

```
attccatttt gagttaattt ctgactatgg ttcaagataa aaaacaaagt tctttttttt     33074
tgcatatgga tatccagttg ctccagcact atttgttgaa aaggctatgc ttttgggtgg     33134
ctcagggttt agcgtctgct ttgggctcag ggcatgatcc cggggtcctg ggatcaagtc     33194
ctacatcagg ctccccaaag gaagcttgct tctccctcta cctatgtctc tgtctctctc     33254
tctgtttctc atgaataaat aaataaataa aatcttaaaa aaaagacta tgctttctct      33314 gttgagtagc cagttgtctc tatatgtcat gggtctattt ctaggctttc tgttctgtgc     33374
cattcattta tttctctgtc tttatgtcag tatcatactg ttttgatcac tgcagcttta     33434
tcataagtct tgataccagg tagtcttggt tttccatctt tgtttctttt ttttttcttt     33494
caaagttgtt taggctattc caggttcttt ctaattccat ataaatttta gaattagctt     33554
gtggatttct acacaatgta gtcgtgctgt atttgtcttg gcaacctatt ctctcctcct     33614
ctgctatcac caccctaaca cttccctact ccctgacctt gcctccaaac aactttacaa     33674
aagaaagcaa aagccaacag agagttctct caactttgtg ctaccaaata tacaaactca     33734
ccttgctttg tttccctcct tcctagaaca ttaaaggaaa caaccatctt cttgcctaaa     33794
gcccacttcc tacctgtgct cagacccttc ctcaactcaa ctcttgaatt atccattatt     33854
ccatctctct tttacatatc cacccctccac ctctcaactg atccttatc agcaacttgt    33914 aggtctaccc caatcttgcc tattttagaa acttggccta ggttcctctc tccccctctc     33974
tttgctcagt cctggcttcc tcctcttctc actctgcttt tcctccctca gcaatctcct    34034
ccatggacac catcacagct tcagtgacca tccatagatg ggactcccaa atgtacatct     34094
ctaaccctca tgtcttctct gagatccaaa ttcatgtatc caattgtcca cttgtcatct     34154
ctccttggac atttctaagg ccccctaaaa tccacatatc cccaaactat aaccctttgcc    34214 ctcctcactg cttccctgac ccatccccctt catggtcacc ctgccagcac cagcatgcat   34274
ctggttgtgc aagccagcta cttcctctct ttccccccaat caatccattg ccagttctca   34334 tttatttttac ctcctaaaca gaatcttcta tttctgtctc tctccttcca agcacaagtc   34394
ctaaacacct ctccacagca gccttacagg ttttcctgggg cctctctgcc cttttcagtg    34454
agtttccaca cagcagccac agtgatcttc ttaaagccag tggcagtgca gcattccccc    34514
ctacctataa gtctttcaag gttttccatga aaccaaaga ccctcaatga tgtctataag    34574
catggtctgg cccctgtagc ctcctcagcc ccatctccca ccaaagtacc cctctccaac    34634
cacactgacc tttagcccct cctcatgctc cctcaaacct gtggcatttg tgtgtgccgt    34694
tcccactgtc tgaaatgctt ctcatcccac cctgaccacc ctctggaacc tcacttgccc    34754
ttcagatctc agttcaaatg ttgctccctc agggaagccc cctcccccc ccgaggaaat     34814 cctccctgct atcatggtcc tttcttgcct aggacttatc ttggttaaaa tgagattatt    34874
tacatagtca atgcctgccc ccatgccaga ctgtaagctc caagaggcca agaaccatca    34934
catctgtttt tgtccacttc actcctcagc gcctgctata atgcgtggca catacagatg    34994
cacaataact atccgttgaa taagtgaatc aatacacaat ataaatttga gcacattctg    35054
cttctgaaaa taatttggga attttttgcaa atttggcatt tttgcaaatg ccagactgat   35114 gtcagggggtt agtaaagcca ccagtgaccc caggctgttg ttttcctag at  gct gct     35171
                                                       Asn Ala Ala
                                                           260 tac atc aat tct ccc tcc aag aga gtg ata ttc ccc cgt gta gaa gtg         35219
Tyr Ile Asn Ser Pro Ser Lys Arg Val Ile Phe Pro Arg Val Glu Val
            265                 270                 275 tac tgc aat ata gaa ctt gcc ctt ggc aac gag tgc cac gaa tgc agt         35267
```

|  |  |  |  |  |  |  |  |  |  |  |  |  |  |
|---|---|---|---|---|---|---|---|---|---|---|---|---|---|
| Tyr | Cys | Asn | Ile | Glu | Leu | Ala | Leu | Gly | Asn | Glu | Cys | His | Glu | Cys | Ser |
|  |  | 280 |  |  |  | 285 |  |  |  | 290 |  |  |  |

```
cag tca agc ctc caa aca cag cag caa gaa tcc ata caa ctt cac aca      35315
Gln Ser Ser Leu Gln Thr Gln Gln Gln Glu Ser Ile Gln Leu His Thr
    295                 300                 305 cag agg gct cct gaa gga gaa gga aag ggc agc cac ggt tca ctt ccg      35363
Gln Arg Ala Pro Glu Gly Glu Gly Lys Gly Ser His Gly Ser Leu Pro
310                 315                 320                 325 tcc tca cct gtg cag aca ccc gga gcc aca tgt gag tgg cct gta gag      35411
Ser Ser Pro Val Gln Thr Pro Gly Ala Thr Cys Glu Trp Pro Val Glu
                330                 335                 340 tca cct gtt tca cca cct gtc cct tca ctt gag cag tca cct gca act      35459
Ser Pro Val Ser Pro Pro Val Pro Ser Leu Glu Gln Ser Pro Ala Thr
            345                 350                 355 cca ctg gct tca tca cca tca cat tct gca gct gac ctg ccc cct gct      35507
Pro Leu Ala Ser Ser Pro Ser His Ser Ala Ala Asp Leu Pro Pro Ala
        360                 365                 370 tcg ctc cca gct gta ccc tta cca ctc agc tca aca ctt gag ctg tca      35555
Ser Leu Pro Ala Val Pro Leu Pro Leu Ser Ser Thr Leu Glu Leu Ser
    375                 380                 385 cgt gta tca cca cag cag cag gta caa act act gga tcg cca cca aga      35603
Arg Val Ser Pro Gln Gln Gln Val Gln Thr Thr Gly Ser Pro Pro Arg
390                 395                 400                 405 tcc cca cct tcc cag tca tct ctg tca cac agg cca ccc ttg ggg cct      35651
Ser Pro Pro Ser Gln Ser Ser Leu Ser His Arg Pro Pro Leu Gly Pro
                410                 415                 420 tca tct gta ggg gca tct caa aca ctg ccc caa cgt tct tct tca gca      35699
Ser Ser Val Gly Ala Ser Gln Thr Leu Pro Gln Arg Ser Ser Ser Ala
            425                 430                 435 tca cct gca cag cca cct gtg gag gaa cta ggc cca gaa cag tcc caa g    35748
Ser Pro Ala Gln Pro Pro Val Glu Glu Leu Gly Pro Glu Gln Ser Gln
        440                 445                 450 gtacagaccc ttctggcttc tcacagcttc cttacgtctg gagcctctca acaagtgtgc    35808
aacaacatgg tagctgataa ccattgcttc ggaggggtgc actggtaaag ttagcagtca    35868
gctttagcag ctctacctat tttgaggata ggccaccaca agggaacagt gttcttgaca    35928
tttgttcatg tctttagtcc agtgattttc aaaggttggt ctctgaccaa cagcgaactc    35988
atcacctggg aatttgttag aaacgaaaat tctcaagccc tactgtagac ctactaactc    36048
agggggtggg acccagctac ctatcttttt tatatgccct ccaggggatt cttttgagaa    36108
ccatgtttgg gaaccactgt aatggaaggt ttttattttg tgataaccac cgtgccaggg    36168
cagtgctact caaagagtgc tctgtggacc agtgctggtc cctaaactat tgttactaa     36228 tttacaatga aatgagcaca gaagttaaaa gtaagcattt agaaatgttt atagccatga    36288
catccaagag tttggtcatt tcttaccag ttcattgtat tgtatttcac aaaagtacta     36348
gtccattatg gattacaaaa aaaaaaaaaa aaagattttt aaaaagctgg ttcttcataa    36408
ctggtttctt ccacagatag tttgagaagc attattctag aggcttcaaa gccacacaat    36468
tctcagctcc tcactctcag aaaatctccc ctccagcaaa ggggatgaca gagataccaa    36528
cctcaaaaat acaagcaaga gtcattaagt acaacattac taaaaagagt attggaaata    36588
tgcatagaga ttaagattac ttctctctgg ggaattaagg aaggcttctt gcagctgaca    36648
ggtgagttga aatgagcaag attttgacca tcatggtttg tgagacagga tgaggcaaag    36708
tagaatgaga agtttaggct ttgttttatcc tagaggctca ggtacggaga gggaacgtgc   36768
aaggtacgtt caggatgaag aggataccctg tttagctact gaggatggtc cgggtggggg   36828
```

```
caacaggaga ggagcccaaa tgatggactg aagccaggtc atagggtctt tatgatccat   36888
ccaccaaatt cccatagtta ttagggtaaa cattagcacc aattagcacg atggtttcct   36948
tcttggcaga tctgccccag gcaggggcac attttctcta gaatagattt gactctttta   37008
atcacggtgg gacaaaaata tcaggacatt aaaagtaagg aaattggccc aagtgtttca   37068
catgctttct tatttgctgt taagcgaaat gcatttctct tatgttattc acacctgtgc   37128
ctaaagtcct cttcaggtag cctgagcaat cctgggccct gagctggcat tccgtgctca   37188
gattggggat agagggaaca gattgtccag tgggtctcaa ctaggagtga ttttgtctcc   37248
cagaagacat ttggcatcaa agacattttt ggttttcacc tagtgggtaa tatctagttg   37308
attgtagatc aacgctgctg aacactgtac aatgcacagc ctcacaacaa agagccatct   37368
ggatcctaca ttcagtagct ctgagatgga ggaaccttgt tacagtcttc aactgagcct   37428
tagtaaggac agcctaggcc atctgtggga gctgagcaga agggagcctc ttcagaggct   37488
agtgtcatct gtcatttagt gatggccatg ttgttgttgg gggtggaagg ggttgcaaaa   37548
aagtttcagg aaacccata agcaagggag cttcaaatag atttgggagt gccagagata   37608
tccaatgtga cccccaaatg aaagaacttc aaatagaact aatatgtttt atattatttt   37668
tatctacaca tattacaaaa ttacatacca acctttatat attatatacc cccatattta   37728
cataaaatat gaaaagcact tacttaagaa caatagtcat gggtgcagca cctgggtggc   37788
tccattggtt aagcattcta ctctggatct cagctcaggt cttgatctca gggtcatgag   37848
ttcaagctcc acattgagct ctatgctgga tgtggagcct acttgaaaaa aaaaaagaac   37908
aatggtcatg aaactagtaa tgttttctat tctgttaaaa aggaagaaag cattatatac   37968
agataaagca ggcgatggaa agttcaggcc cttagggggg acttttcctg aaaactcaca   38028
ctaaagggct gttttttgtg agggaattgt tgataacatt gcattaattg ataaattaca   38088
tcgattattg ataacattac atcaaagatc agcatctgtc ctgccacaga tgccactgcc   38148
ctgggtctca gtcaaatcca acaacgtggt tctggtccta aacatgagac tttgagatta   38208
agagagctgt ttattgtttc tggacactct cacttacttc ctattttat ttcaaaaatg   38268
actaagtcct cttccctgac cttacctcac tcgtgtctct tattttgac tgcag ct      38325
                                                                Ala
ccc ctt gcc tct tca aag cca gaa ggt acc aca cct ttg gtt aat gtg     38373
Pro Leu Ala Ser Ser Lys Pro Glu Gly Thr Thr Pro Leu Val Asn Val
455                 460                 465                 470 aag gaa gcc acc agc aag cct cat gca at   gtaaatttct ccttaatcgt      38422
Lys Glu Ala Thr Ser Lys Pro His Ala Met
                475 gacacattct ttcctttggc tgagggtggg ggaagtaggg gggagggtag ctaagtgaaa   38482
atttcctttt ctttagttgc gctagaaaca ctgggatcct tttccagttt gtgtgattac   38542
attccaagcc tttacattct ctcttcttca gtggggcaa cgaatgggaa atgagttatt   38602
catgctcaca gtgtcattct cttcatctcc ttgctgtgcc ccctgggaa tgtgccttct   38662
ctgagtgtag taggagaaca tgcaccccct catgtcttat tctctggtag tgtctcagtt   38722
caagggagct agcaggcatg ctacatacta gcctgaggta ggctatttcc tgcatggtac   38782
gaattgtgag actctatcaa aggcctcctt taatccaaat gattttctat caacacagta   38842
agagggctga tattgctatg ttgtagattg tcccccagaaa atctttttta taacacacat   38902
caattgtctg gattgtgtaa catgttctcc attacttagc ttcacagtca ttctgagagg   38962
cctgaggatt agtatatttt ttaagattta tttttattta tacgagagag agcacacata   39022
```

```
ctgcatttgc aagcacaagg atggggaagg gagagggtg tgtaggagca gagggagagg    39082
gagagggaga cctatgcaga ctccgcaatg agtacggagc cccatgtagg gctctatctc    39142
atgaccctga gatctcgacc tgagccgaaa ccaagagtca aagggccaac caactatgcc    39202
acccagtgcc ccaggattgg tattttttaag ttccttgggg accacattac ccaggctccc   39262
ttgctggctt cttgttagtt gggttagcca gtagaaggca ccagcaggag attagaagat    39322
gggctaaaga atatctctcc cctttcccaa cctcatcctt cccgccttgg gcagttctgg    39382
caatgactat tccatggcca tggctgcagc tattgggaga gcaggtcctt ttgatgttcc    39442
aactccatat catcaaatat attaaaacat acctgcttct cacattaagt atcactttaa    39502
ttataaaact ttttgaggag cagctgggtg gctcagttgg ttaagcatct gccttcagct    39562
caggtcatga tcccagggcc ctgggattga gccccacatc aggctccctg ctcagccagg    39622
aacctgctgt gcttgcttgc tctctctctc taataaataa ataaactctc tctcaaaaaa    39682
aaaaaagact tttcgtaaga gtttgcataa atttaagaat tttgtgctcg gcatatact     39742 atgcgttttg ttcacatggt ttaaacttta ttgcattgac attgaactta taaaagttta    39802
attgagtttc agttgactag ttggcatgat gttacttaga taaatagtca ttggttataa    39862
aacgaatatt tgctgtggaa ctctggtgtc agccagggtt aaaagccata acattggctt    39922
gtctgtctac cttctgagct ggagcagggc cctgatagtg aaggacacag gacgggtcat    39982
taacaaacta tttacttcat ctattgccca g g gga aac cct act gaa gac tcc    40035
                                    Gly Asn Pro Thr Glu Asp Ser
                                                        485 agt tgg atg agc aag gtg ttc aag aag aac aaa caa aag aca agt agc      40083
Ser Trp Met Ser Lys Val Phe Lys Lys Asn Lys Gln Lys Thr Ser Ser
    490                 495                 500 acc aga aaa ggc ttc cca aga cac cca cga tcc aaa aaa aca ggc ggc      40131
Thr Arg Lys Gly Phe Pro Arg His Pro Arg Ser Lys Lys Thr Gly Gly
505                 510                 515 aaa gtg ca  gtgagcatga ctaatgtttt tcgaaatcca cggggaggaa               40179
Lys Val Gln
520 aagctccggg aagagtctgc aggaagatca caaggggcag aggaagaatc agcaggagca    40239 ggtgttagga gctggacttt ggagtcagac ccacccaata taaactccct gctctgccat    40299 aatcttgctc agtgatcatg cttaggacat atggtctttc taagcctcta tttcctgatc    40359 tgtaaaatag ggataatatt gtgagggttt aatgaggcca acatgtaaat ttctttgcag    40419 aatgcaagat gtgtaatcag cactcaataa cttagtaggt attagggtta tatgcagagg    40479 ttaactacct gcttctcagt ttctgaatag aactctattt acaaaccaaa ctaaacagat    40539 gtgtgactgt gtgaccctca gcatatagag atcctaactg ttgccaagct acaactaaaa    40599 gccctaacca atgtaagcct gcttcttaca gcttttttat tatattatat tgtcattgat    40659 ccatcaatta actttgattg agcacctaat gagtgccaac cactcttctg ggctctagag    40719 atagtaaaga ttaattgaat tcaatctctg acttttttaaa aaacatttta tttatttatt   40779 tgagagagaa gagagagatt acagagggag agggagaaac aaagattccc tgctgagcag    40839 agcctgacac agggctcgat tccagcatcc tgggatcatg ccctgaagcc aaaggcagac    40899 atttaaccaa ctgagctacc caggcacccc ttgatcctta acttttaaaa ggttacccca    40959 aaattgaact taagaccaaa gacaataacc aagttttaat tttttattga aatataacat    41019 tgtttttttaa agggacatgc atatatacat acatacttac aaatgaaaaa tgccagcttc   41079 aaacaaacca agccagggat catctacaac tattttattg gattgtcaaa atattctctg    41139
```

```
aatggaacag acccacactg ctatctactt tgcttcaagc ttccattggt cagaaaaatc   41199
cctagattat tctaagcgac aaccttctgt attgttcctt tcccaggtgg ggatcccagg   41259
tgagcagaga gctgtatcag ggagatgagg gtcagaagct tgccctagca tctcaagttc   41319
actttgaggt ctgggcaagt aggtacttgg tgggtggtgg gaaggagatt ctcaggaatc   41379
cactgcagga agtggggcag atgcatgtgt tactttctgg attaaaggac aggcagggaa   41439
ggtgcaggac ccagtgggca gttggcagtc tccttggggg tcatgaaatt agtgaatcct   41499
ggaattagtt tcactctgtt ccttggtatc cagccccaag tcttctttga cttttgagcg   41559
tctgtatctc tgttgctagg agctcaaggt caatttggc caagagacca tgggcaggtc   41619
tgctgtgggg gtggggaagc ttccttggag ctgggagtgc catctggaag ccaggctcag   41679
agttaagtcc cttcattcca gagccaggct tcctcctata catcggagca ggggaacta   41739 tgtaattcag ccatagctac cctggtcgtt aaatttctaa gaatcaaggt gctttataaa   41799
gaagaaggct atgataaaaa caaacaaaac aacattcaca gctgtgggaa acactgttgt   41859
cagtaggtca cacattctgt ctgcggcatt cctttataga acagattacg aaactgcctg   41919
gaagcaattt accaattgat ggtctcaagc aattccatgc aaattcactg ctctgagctt   41979
caaagaccag ggtaggggta gggggtaga aaagacaagt tgaaaaggt taggcataga   42039 agaggagtga tccagaaaga gagaaatctg ctcatttcct cccagagtat aatcacaaga   42099
gagatggtca catccatggg ctagtcctgt gcaactcctg gcccccagct gatattcctc   42159
ccaataaaga ggagagaagc tagaataaaa gctacagagt agatgttcca tacattaatc   42219
tctctctctc tctgtttctt aaagattttta tttatttatt tatttatta tttatttatt   42279 tatttgagag cagagagaac cagtgggaag ggggagtaga gggagaagga gagaatctca   42339
actagactcc atcctgagca tggagcctga cccagagctc aatgcagagc tccatgatac   42399
gaccctgaga tatgacctga gccaaaatca agagtctgac acttagggga tccctgggtg   42459
gcgcagcggt ttggcgcctg cctttggccc agggcgcaat cctggagacc cgggatcaaa   42519
tcccacgtcg ggctccctgc acggagcctg cttctctctc tgcctgtgtc cctgcctttc   42579
tctctctctc tctgtgacta tcataaataa gtaaaaattt aaaaaaatat atccatattt   42639
aagagtctga cacttaatca accaagcctc ccaggtgccc ctccttctgt gttttttaag   42699
tcagatgttc aagttcatac tctgatgctg gttattttag tgagtagttg ctgtttata   42759 atgctaccta acaaacaccc ctctccatct caatgggtta caaagcaaat gtttattttg   42819
ctctttcaga gttctgtgac ttgtctggga tagctctgct taggctactg gttggggtcg   42879
agtttgatcc ctgtcccttt cattccagga ccagcagatg tgccagatat gctctgcctc   42939
tggatcatgg ctagatacat gtctcagcct ggctttcctc tgctagtttg tctctcctcc   42999
agtcagattt cagcagtcgt ctgatccggg ttgtgtaact ggcctcaaag tggcaagaca   43059
gattgagaaa ttcagggact gcctacggct acaaatggaa aaggaggagg tcccacttgc   43119
taactgccac tcaaatcctc tggactgcta ctgtctgtca gactcctcga atttctaaca   43179
tttctacagc tagaaagccc ctccttttag ttactatgga atttccccct attcaaatga   43239
gaatgtgatg ataatagcta aaacttagag tagttattat gttccaggca ttgtggtaca   43299
gagagggtaa gcaacatgcc caaagtcaca cagtaggtaa tgacagagcc aggatccgaa   43359
tccaagttgt ctgtcaccag catcttggtg tcaagcacta agtgatatag ccttccaggg   43419
taggagcacc agagtgcatc ggaagtcaca gggtctagtc ctagattgtc tgtttggcag   43479
```

```
ggagggtgca cttggaggtg cacagacacg gcagggatag cttgggtgcc atgctaacaa    43539
ggttggacct cacctgtggt gctggggaga catcacaggg tttaaacaga atgacatggt    43599
cagatttgaa aaccatccaa gaatgtaccg tgtacagtgc acacgccaac atttctctga    43659
ggtggactct gcaggaggct tcctacaata tccttgagag ggccaatgac tggccagggc    43719
cacacagcaa gtggaagagg ccttgaaact cagggcttcc cattggcccc cttgtctcat    43779
ttgtcctcac acatgctttc ttggcttttc acatccag g tct gct ccc tgt ccc      43833
                                           Ser Ala Pro Cys Pro
                                                            525 ctc gac ttc act ctg ctc tcc act tcc gag aca gtt tgg gtc acc tac      43881
Leu Asp Phe Thr Leu Leu Ser Thr Ser Glu Thr Val Trp Val Thr Tyr
            530                 535                 540 agg cct cat ccc agc cag atc cag gaa cac agc tgt cct gag              43923
Arg Pro His Pro Ser Gln Ile Gln Glu His Ser Cys Pro Glu
    545                 550                 555 gtatggaact gtccagcatc accctggagg ccacacacga cctgctctgt ccccatatgc    43983
tgcggtgacc tctgagcact gttgacccag tttcctttct gaccccacct gcctcttcct    44043
ggtcacagtc aaggccaacc ctagcgcata tagttactca tgtactaaga aaacagtacc    44103 cttttccgaaa gaacttgatt gcgagctgct ggatgatctt gataatacac tgattttgtt    44163
aaaacagttg actgccacct gctagaaatc tgtatgaacg acatataaag ctacaaaacg    44223
gtacacataa catacaaaac tgtacaaata acatgtggca taaataggtc catgatatgt    44283
ggccccgttg cattggcagt ttctccttgt acagtgtaca gtctgtacaa ctgcacaact    44343
cagcactctg gaggccattc cacttctttt cccttctcga aaagccaagt attaaccaga    44403
cttttgtaaa tctaataatg tttcaaacac tcttttatct actcctgctc tgcaaatgga    44463
attctccatt tgcaaacaaa aacaaaaaca caacaaacaa acacacacac acaccccaca    44523
aaaaaacctc ttgtataaca gtgggatttg ctaactgact ttttggtata gattgagatt    44583
tccaatttac acacatcaag ttggctataa tggggcctgg ctacttgctt ggggctgccc    44643
gaggcatagg aagctatgag ggatgttctc agcggaaata aggggaggaa agtcctagat    44703
gagggactta gaaatgatgc atctctgtcc tttttctag gaa gct gtg aac caa      44757
                                             Glu Ala Val Asn Gln
                                                              560 gag aga act tga gctggaatga aagagaacct gttgaccgca aggtagagcc          44809
Glu Arg Thr
        565 ttctccccaa ggctctcaga cacattctct tcacctaggc cttttgggga tcagatgtca    44869 cccacgacca agcctgttcg tgcagagggt cctgcttctc ctggtcaagc acctccttgt    44929 ctgaacaatc tctcagcttc tctgcggtcc tccagccctt ccactactct gctctggaca    44989 gatagatgga caccaacatg gataggctct gaagagccca cagcacatcc tgctcccatc    45049 tggctgggct ctgggccttc ctcccagccc agcctgagtt tgcttcttcg agatggacca    45109 catcaattct ggcccacccg ggatctagtc tacagggcca agctcttggg ggttgagcaa    45169 gactgagcat ggatgcactt tcctcttttcc tgtggtgtca agagactgag ctctttggtt    45229 ttgtcttgtt tttcattctc aagtgtacca aaggcttgat                          45269

<210> SEQ ID NO 6
<211> LENGTH: 18
<212> TYPE: DNA
<213> ORGANISM: Artificial
<220> FEATURE:
<223> OTHER INFORMATION: primer
```

```
<400> SEQUENCE: 6
cgggctagca ggagagtg                                              18

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
gctctgtttc ccaaagcatc                                            20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
ttctagggtt tcccgtgttg                                            20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
aagaatgggg gactgtttcc                                            20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
tctggtcccc ataacagtgc                                            20

<210> SEQ ID NO 11
<211> LENGTH: 19
<212> TYPE: DNA
<213> ORGANISM: Artificial
<220> FEATURE:
<223> OTHER INFORMATION: primer

<400> SEQUENCE: 11
agagcactcc tgggtcctg                                             19

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
tgtcccaagg gactcatttc                                            20

<210> SEQ ID NO 13
```

-continued

```
<211> LENGTH: 20
<212> TYPE: DNA
<213> ORGANISM: Artificial
<220> FEATURE:
<223> OTHER INFORMATION: primer

<400> SEQUENCE: 13
acacaaatgg aaatgcatgg                                            20

<210> SEQ ID NO 14
<211> LENGTH: 18
<212> TYPE: DNA
<213> ORGANISM: Artificial
<220> FEATURE:
<223> OTHER INFORMATION: primer

<400> SEQUENCE: 14
caagggccat gaggtgag                                              18

<210> SEQ ID NO 15
<211> LENGTH: 20
<212> TYPE: DNA
<213> ORGANISM: Artificial
<220> FEATURE:
<223> OTHER INFORMATION: arti

<400> SEQUENCE: 15
ggcatctcgg gttctctttt                                            20

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
ccagactgat gtcaggggtt a                                          21

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
cttggtggcg atccagtagt                                            20

<210> SEQ ID NO 18
<211> LENGTH: 18
<212> TYPE: DNA
<213> ORGANISM: Artificial
<220> FEATURE:
<223> OTHER INFORMATION: primer

<400> SEQUENCE: 18
gcttcgctcc cagctgta                                              18

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
```
tggcctatcc tcaaaatagg taga                                    24

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
actgaagcca ggtcataggg                                         20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
atgcatttcg cttaacagca                                         20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
gacagcctag gccatctgtg                                         20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
gttctttcat ttgggggtca                                         20

<210> SEQ ID NO 24
<211> LENGTH: 24
<212> TYPE: DNA
<213> ORGANISM: Artificial
<220> FEATURE:
<223> OTHER INFORMATION: primer

<400> SEQUENCE: 24
agagctgttt attgtttctg gaca                                    24

<210> SEQ ID NO 25
<211> LENGTH: 19
<212> TYPE: DNA
<213> ORGANISM: Artificial
<220> FEATURE:
<223> OTHER INFORMATION: primer

<400> SEQUENCE: 25
ctacttcccc caccctcag                                          19

<210> SEQ ID NO 26
<211> LENGTH: 20
<212> TYPE: DNA

```
<213> ORGANISM: Artificial
<220> FEATURE:
<223> OTHER INFORMATION: primer

<400> SEQUENCE: 26
ggccctgata gtgaaggaca                                           20

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
tcctaacacc tgctcctgct                                           20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
caagtggaag aggccttgaa                                           20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
ctgggtcaac agtgctcaga                                           20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
cggaaataag gggaggaaag                                           20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
ttgaccagga gaagcaggac                                           20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
ggaagagcag gtgttcaagg                                           20
```

```
<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
cgatgagctc ttccttggat                                                     20

<210> SEQ ID NO 34
<211> LENGTH: 19
<212> TYPE: DNA
<213> ORGANISM: Artificial
<220> FEATURE:
<223> OTHER INFORMATION: primer34

<400> SEQUENCE: 34
cttctccggc agtggattt                                                      19

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
gtggcgacct tgtaggagtc                                                     20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
acggagagag tgtcgtggtt                                                     20

<210> SEQ ID NO 37
<211> LENGTH: 19
<212> TYPE: DNA
<213> ORGANISM: Artificial
<220> FEATURE:
<223> OTHER INFORMATION: primer

<400> SEQUENCE: 37
ataggtctgg cgggaacag                                                      19

<210> SEQ ID NO 38
<211> LENGTH: 19
<212> TYPE: DNA
<213> ORGANISM: Artificial
<220> FEATURE:
<223> OTHER INFORMATION: primer

<400> SEQUENCE: 38
ggggacagat gtcttgctg                                                      19

<210> SEQ ID NO 39
<211> LENGTH: 20
<212> TYPE: DNA
<213> ORGANISM: Artificial
<220> FEATURE:
```

```
<223> OTHER INFORMATION: primer

<400> SEQUENCE: 39
gaaaacatcg ccaggatgac                                              20

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
tcttgctgct gtgtttggag                                              20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
cagtcaagcc tccaaacaca                                              20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
ggcctagttc ctccacaggt                                              20

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
cacctgtgga ggaactaggc                                              20

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
cttggttcac agcttcctca                                              20

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
tcacgtgtat caccacagca                                              20
```

```
<210> SEQ ID NO 46
<211> LENGTH: 27
<212> TYPE: DNA
<213> ORGANISM: Artificial
<220> FEATURE:
<223> OTHER INFORMATION: primer

<400> SEQUENCE: 46
tccaactgga gtcttcagta gtagtag                                              27

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47
tcacgtgtat caccacagca                                                      20

<210> SEQ ID NO 48
<211> LENGTH: 23
<212> TYPE: DNA
<213> ORGANISM: Artificial
<220> FEATURE:
<223> OTHER INFORMATION: primer

<400> SEQUENCE: 48
ccaactggag tcttcagtag ggt                                                  23

<210> SEQ ID NO 49
<211> LENGTH: 18
<212> TYPE: DNA
<213> ORGANISM: Artificial
<220> FEATURE:
<223> OTHER INFORMATION: primer

<400> SEQUENCE: 49
gctttcccct ccatcgtg                                                        18

<210> SEQ ID NO 50
<211> LENGTH: 22
<212> TYPE: DNA
<213> ORGANISM: Artificial
<220> FEATURE:
<223> OTHER INFORMATION: primer

<400> SEQUENCE: 50
gtgttgaaag tctcgaacat ga                                                   22
```